United States Patent
Domke et al.

(10) Patent No.: US 9,641,569 B2
(45) Date of Patent: May 2, 2017

(54) SYSTEMS AND METHODS FOR COLLABORATING IN A NON-DESTRUCTIVE TESTING SYSTEM USING LOCATION INFORMATION

(71) Applicant: General Electric Company, Schenectady, NY (US)

(72) Inventors: Michael Christopher Domke, Skaneateles, NY (US); Sekhar Soorianarayanan, Bangalore (IN); Thomas Eldred Lambdin, Auburn, NY (US); Robert Carroll Ward, Essex, CT (US); Scott Leo Sbihli, Lexington, MA (US)

(73) Assignee: General Electric Company, Schenectady, NY (US)

( * ) Notice: Subject to any disclaimer, the term of this patent is extended or adjusted under 35 U.S.C. 154(b) by 663 days.

(21) Appl. No.: 13/747,456

(22) Filed: Jan. 22, 2013

(65) Prior Publication Data
US 2014/0207862 A1   Jul. 24, 2014

(51) Int. Cl.
*G06F 15/16*   (2006.01)
*H04L 29/06*   (2006.01)
(Continued)

(52) U.S. Cl.
CPC ........... *H04L 65/403* (2013.01); *G06Q 10/06* (2013.01); *G01N 23/04* (2013.01); *G01N 27/9046* (2013.01); *G01N 29/44* (2013.01)

(58) Field of Classification Search
CPC .................................................... G01N 29/069
See application file for complete search history.

(56) References Cited

U.S. PATENT DOCUMENTS 6,317,039 B1   11/2001   Thomason
6,830,545 B2   12/2004   Bendall
(Continued)

FOREIGN PATENT DOCUMENTS

GB      2449754 A      12/2008

OTHER PUBLICATIONS

International Search Report and Written Opinion issued in connection with corresponding PCT Application No. PCT/US2013/074332 on Oct. 30, 2014.
(Continued)

*Primary Examiner* — Umar Cheema
*Assistant Examiner* — Tesfu Mekonen
(74) *Attorney, Agent, or Firm* — Fletcher Yoder PC

(57) ABSTRACT

A collaboration system for sharing data in a non-destructive testing (NDT) system may include a first computing device that may receive data that has been acquired using one or more NDT inspection devices. The first computing device may then establish a communication connection between itself and some other computing device such that the communication connection may enable the first computing device to share data with the other computing device. After establishing the communication connection, the first computing device may determine location information that corresponds to the data. Using the location information, the first computing device may then determine one or more assets that correspond to the data. The first computing device may then identify information associated with the assets and display the information.

20 Claims, 17 Drawing Sheets

(51) Int. Cl.
*G06Q 10/06* (2012.01)
*G01N 27/90* (2006.01)
*G01N 29/44* (2006.01)
*G01N 23/04* (2006.01)

(56) References Cited

U.S. PATENT DOCUMENTS

| | | | |
|---|---|---|---|
| 8,059,882 B2 | 11/2011 | Amidi | |
| 8,108,168 B2 | 1/2012 | Sharp et al. | |
| 8,255,170 B2* | 8/2012 | Kollgaard et al. | 702/34 |
| 8,299,785 B2* | 10/2012 | Bousquet | G01N 27/9033 324/220 |
| 8,695,802 B2* | 4/2014 | Pirmann | 206/455 |
| 8,712,716 B2* | 4/2014 | Thomas et al. | 702/104 |
| 2002/0198997 A1 | 12/2002 | Linthicum et al. | |
| 2008/0300748 A1* | 12/2008 | Drummy et al. | 701/35 |
| 2012/0271824 A1 | 10/2012 | Goldfine et al. | |
| 2012/0327187 A1* | 12/2012 | Troy et al. | 348/46 |
| 2013/0340531 A1* | 12/2013 | Hutchinson et al. | 73/633 |
| 2015/0032387 A1* | 1/2015 | Froom et al. | 702/33 |

OTHER PUBLICATIONS

U.S. Appl. No. 13/747,435, filed Jan. 22, 2013, Jason Howard Messinger.
U.S. Appl. No. 13/747,438, filed Jan. 22, 2013, Jason Howard Messinger.
U.S. Appl. No. 13/747,457, filed Jan. 22, 2013, Jason Howard Messinger.
U.S. Appl. No. 13/747,453, filed Jan. 22, 2013, Sekhar Soorianarayanan.
U.S. Appl. No. 13/747,429, filed Jan. 22, 2013, Sekhar Soorianarayanan.
U.S. Appl. No. 13/747,464, filed Jan. 22, 2013, Sekhar Soorianarayanan.
U.S. Appl. No. 13/747,443, filed Jan. 22, 2013, Jason Howard Messinger.
U.S. Appl. No. 13/747,449, filed Jan. 22, 2013, Michael Christopher Domke.
U.S. Appl. No. 13/747,416, filed Jan. 22, 2013, Michael Christopher Domke.
U.S. Appl. No. 13/747,408, filed Jan. 22, 2013, Michael Christopher Domke.
U.S. Appl. No. 13/800,015, filed Mar. 13, 2013, Kevin Andrew Coombs.
U.S. Appl. No. 13/732,238, filed Dec. 31, 2012, Michael Christopher Domke.
U.S. Appl. No. 13/732,252, filed Dec. 31, 2012, Kevin Andrew Coombs.
U.S. Appl. No. 13/732,261, filed Dec. 31, 2012, Eugene Schiefer.
U.S. Appl. No. 13/732,281, filed Dec. 31, 2012, Jason Howard Messinger.
U.S. Appl. No. 13/732,293, filed Dec. 31, 2012, Jason Howard Messinger.
U.S. Appl. No. 13/732,303, filed Dec. 31, 2012, Thomas Eldred Lambdin.
U.S. Appl. No. 13/732,268, filed Dec. 31, 2012, Scott Leo Sbihli.
U.S. Appl. No. 13/732,309, filed Dec. 31, 2012, Jason Howard Messinger.
U.S. Appl. No. 13/732,272, filed Dec. 31, 2012, Jason Howard Messinger.
U.S. Appl. No. 13/732,319, filed Dec. 31, 2012, Michael Christopher Domke.
U.S. Appl. No. 13/732,327, filed Dec. 31, 2012, Michael Christopher Domke.
Sorrel, Charlie. iControlPad Ships at Last [online], [retrieved on Mar. 21, 2013]. Retrieved from the Internet <URL: http://www.wired.com/gadgetlab/2011/11/icontrolpad-ships-at-last/>.
OmniScan MX [online]. p. 5. Olympus, 2010 [retrieved on Mar. 28, 2013]. Retrieved from the Internet: <URL: www.olympus-ims.com/en/omniscan-mx/>.
Georgeson, Gary. [online], [retrieved on Mar. 28, 2013]. http://www.meetingdata.utcdayton.com/agenda/airworthiness/2012/proceedings/presentations/P5526.pdf.
Phasor XS User's Manual [online]. General Electric: Measurement & Control Solutions. [retrieved on Mar. 28, 2013]. Retrieved from the Internet: <URL: www.ge-mcs.com/download/ultrasound/portable-flaw-detectors/Phasor%20Series/om-phasor-en_rev10.pdf>.
USM Vision 1.2—A Total Weld Inspection Solution to Increase Productivity in New Process Pipework Fabrication [online]. General Electric: Measurement & Control. [retrieved on Mar. 28, 2013]. Retrieved from the Internet: <URL: www.ge-mcs.com/download/ultrasound/portable-flaw-detectors/usm-vision/GEIT-USMVision-20058EN_LR.pdf>.

* cited by examiner

SYSTEMS AND METHODS FOR COLLABORATING IN A NON-DESTRUCTIVE TESTING SYSTEM USING LOCATION INFORMATION

BACKGROUND

The subject matter disclosed herein relates to non-destructive testing (NDT) systems, and particularly to systems and methods for sharing NDT data with various parties.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions.

In a conventional NDT system, data may be shared with other NDT operators or personnel using portable memory devices, paper, of through the telephone. As such, the amount of time to share data between NDT personnel may depend largely on the speed at which the physical portable memory device is physically dispatched to its target. Accordingly, it would be beneficial to improve the data sharing capabilities of the NDT system, for example, to more efficiently test and inspect a variety of systems and equipment.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a collaboration system may include a first computing device that may receive data that has been acquired using one or more non-destructive testing (NDT) inspection devices and establish a communication connection between the first computing device and the at least one other computing device such that the communication connection may share data depicted on the computing device with the at least one other computing device. After establishing the communication connection, the first computing device may determine location information that corresponds to the data, determine one or more assets that correspond to the data based on the location information, identify information associated with the assets, and display the information.

In another embodiment, a computing device may include program instructions that may receive data that has been acquired using one or more non-destructive testing (NDT) inspection devices and establish a communication connection between the computing device and at least one other computing device in a computing network. The program instructions may then determine location information that corresponds to the data, determine one or more assets that correspond to the data based on the location information, and retrieve information associated with the assets from a database that may be communicatively coupled to the computing network.

In yet another embodiment, a non-transitory computer readable medium may include instructions that may receive data that has been acquired using one or more non-destructive testing (NDT) inspection devices and establish a communication connection with at least one other computing device in a computing network such the communication connection is configured to share the data with the at least one other computing device. The instruction may then determine location information that corresponds to the data, determine one or more assets that correspond to the data based on the location information, and display one or more data fields associated with the assets. The one or more data fields may receive one or more entries associated with the one or more assets.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
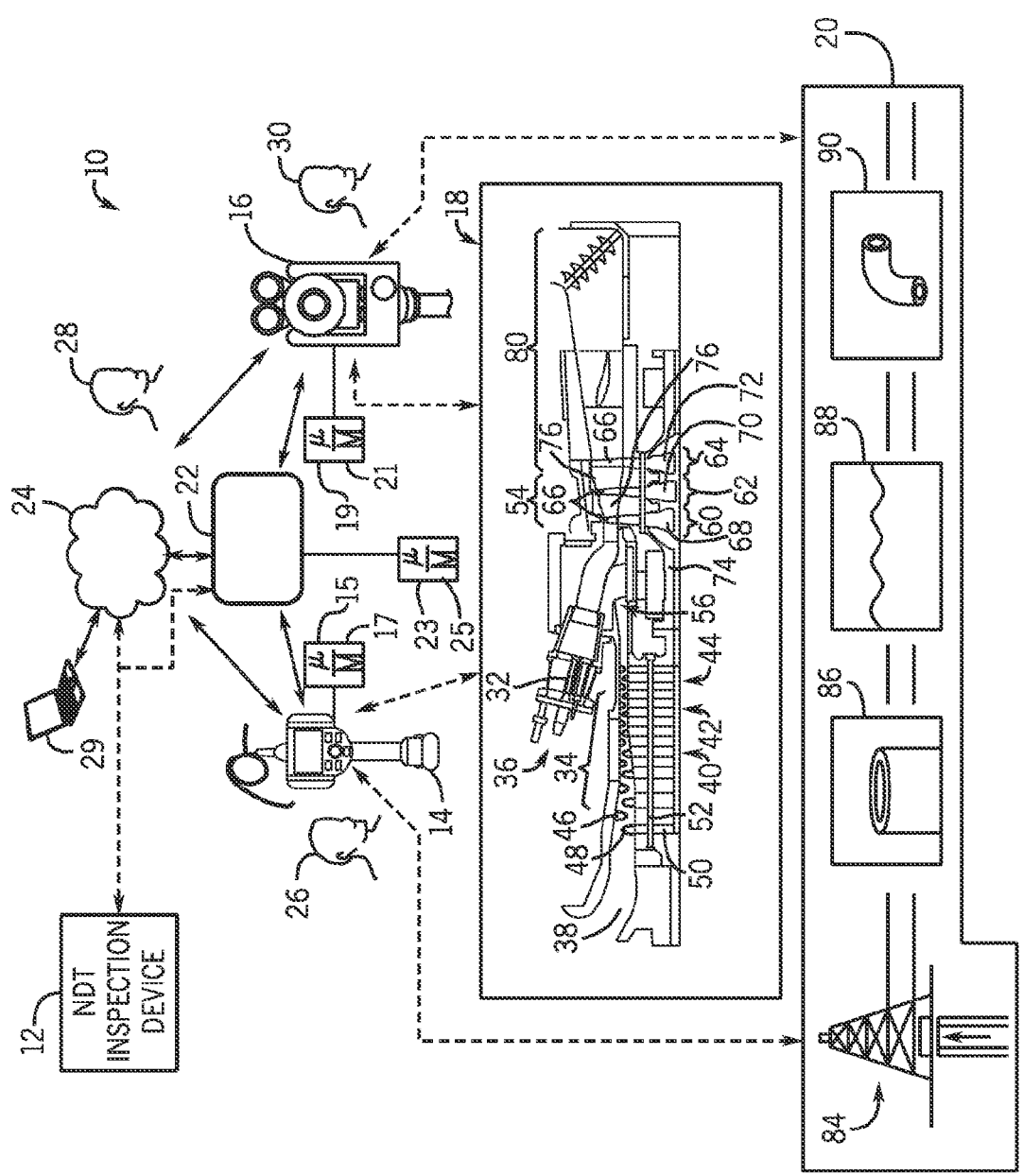
FIG. 1 is a block diagram illustrating an embodiment of a distributed non-destructive testing (NDT) system, including a mobile device.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection and testing techniques, including non-destructive testing (NDT) or inspection systems. In the NDT system, certain techniques such as borescopic inspection, weld inspection, remote visual inspections, x-ray inspection, ultrasonic inspection, eddy current inspection, and the like, may be used to analyze and detect a variety of conditions, including but not limited to corrosion, equipment wear and tear, cracking, leaks, and so on. The techniques described herein provide for improved NDT systems suitable for borescopic inspection, remote visual inspections, x-ray inspection, ultrasonic inspection, and/or eddy current inspection, enabling enhanced data gathering, data analysis, inspection/testing processes, and NDT collaboration techniques.

The improved NDT systems described herein may include inspection equipment using wireless conduits suitable for communicatively coupling the inspection equipment to mobile devices, such as tablets, smart phones, and augmented reality eyeglasses; to computing devices, such as notebooks, laptops, workstations, personal computers; and to "cloud" computing systems, such as cloud-based NDT ecosystems, cloud analytics, cloud-based collaboration and workflow systems, distributed computing systems, expert systems and/or knowledge-based systems. Indeed, the techniques described herein may provide for enhanced NDT data gathering, analysis, and data distribution, thus improving the detection of undesired conditions, enhancing maintenance activities, and increasing returns on investment (ROI) of facilities and equipment.

In one embodiment, a tablet may be communicatively coupled to the NDT inspection device (e.g., borescope, transportable pan-tilt-zoom camera, eddy current device, x-ray inspection device, ultrasonic inspection device), such as a MENTOR™ NDT inspection device, available from General Electric, Co., of Schenectady, N.Y., and used to provide, for example, enhanced wireless display capabilities, remote control, data analytics and/or data communications to the NDT inspection device. While other mobile devices may be used, the use of the tablet is apt, however, insofar as the tablet may provide for a larger, higher resolution display, more powerful processing cores, an increased memory, and improved battery life. Accordingly, the tablet may address certain issues, such as providing for improved visualization of data, improving the manipulatory control of the inspection device, and extending collaborative sharing to a plurality of external systems and entities.

Keeping the foregoing in mind, the present disclosure is directed towards sharing data acquired from the NDT system and/or control of applications and/or devices in the NDT system. Generally, data generated from the NDT system may be automatically distributed to various people or groups of people using techniques disclosed herein. Moreover, content displayed by an application used to monitor and/or control devices in the NDT system may be shared between individuals to create a virtual collaborative environment for monitoring and controlling the devices in the NDT system.

By way of introduction, and turning now to FIG. 1, the figure is a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 15 and a memory 17, and a transportable pan-tilt-zoom (PTZ) camera 16 having one or more processors 19 and a memory 21. In this first category of visual inspection devices, the bore scope 14 and PTZ camera 16 may be used to inspect, for example, a turbo machinery 18, and a facility or site 20. As illustrated, the bore scope 14 and the PTZ camera 16 may be communicatively coupled to a mobile device 22 also having one or more processors 23 and a memory 25. The mobile device 22 may include, for example, a tablet, a cell phone (e.g., smart phone), a notebook, a laptop, or any other mobile computing device. The use of a tablet, however, is apt insofar as the tablet provides for a good balance between screen size, weight, computing power, and battery life. Accordingly, in one embodiment, the mobile device 22 may be the tablet mentioned above, that provides for touchscreen input. The mobile device 22 may be communicatively coupled to the NDT inspection devices 12, such as the bore scope 14 and/or the PTZ camera 16, through a variety of wireless or wired conduits. For example, the wireless conduits may include WiFi (e.g., Institute of Electrical and Electronics Engineers [IEEE] 802.11X), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 22 may be communicatively coupled to the NDT inspection devices 12, such as the borescope 14 and/or the PTZ camera 16, through the "cloud" 24. Indeed, the mobile device 22 may use the cloud 24 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in one embodiment, the mobile device 22 may provide "hot spot" functionality in which mobile device 22 may provide wireless access point (WAP) functionality suitable for connecting the NDT inspection devices 12 to other systems in the cloud 24, or connected to the cloud 24, such as a computing system 29 (e.g., computer, laptop, virtual machine(s) [VM], desktop, workstation). Accordingly, collaboration may be enhanced by providing for multi-party workflows, data gathering, and data analysis.

For example, a borescope operator 26 may physically manipulate the borescope 14 at one location, while a mobile device operator 28 may use the mobile device 22 to interface with and physically manipulate the bore scope 14 at a second location through remote control techniques. The second location may be proximate to the first location, or geographically distant from the first location. Likewise, a camera operator 30 may physically operate the PTZ camera 16 at a third location, and the mobile device operator 28 may remote control PTZ camera 16 at a fourth location by using the mobile device 22. The fourth location may be proximate to the third location, or geographically distant from the third location. Any and all control actions performed by the operators 26 and 30 may be additionally performed by the operator 28 through the mobile device 22. Additionally, the operator 28 may communicate with the operators 26 and/or 30 by using the devices 14, 16, and 22 through techniques such as voice over IP (VOIP), virtual whiteboarding, text messages, and the like. By providing for remote collaboration techniques between the operator 28 operator 26, and operator 30, the techniques described herein may provide for enhanced workflows and increase resource efficiencies. Indeed, nondestructive testing processes may leverage the communicative coupling of the cloud 24 with the mobile device 22, the NDT inspection devices 12, and external systems coupled to the cloud 24.

In one mode of operation, the mobile device 22 may be operated by the bore scope operator 26 and/or the camera operator 30 to leverage, for example, a larger screen display, more powerful data processing, as well as a variety of interface techniques provided by the mobile device 22, as described in more detail below. Indeed, the mobile device 22 may be operated alongside or in tandem with the devices 14 and 16 by the respective operators 26 and 30. This enhanced flexibility provides for better utilization of resources, including human resources, and improved inspection results.

Whether controlled by the operator 28, 26, and/or 30, the borescope 14 and/or PTZ camera 16 may be used to visually inspect a wide variety of equipment and facilities. For example, the bore scope 14 may be inserted into a plurality of borescope ports and other locations of the turbomachinery 18, to provide for illumination and visual observations of a number of components of the turbomachinery 18. In the depicted embodiment, the turbo machinery 18 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 18 (e.g., gas turbine) may include a variety of components that may be inspected by the NDT inspection devices 12 described herein.

With the foregoing in mind, it may be beneficial to discuss certain turbomachinery 18 components that may be inspected by using the embodiments disclosed herein. For example, certain components of the turbomachinery 18 depicted in FIG. 1, may be inspected for corrosion, erosion, cracking, leaks, weld inspection, and so on. Mechanical systems, such as the turbomachinery 18, experience mechanical and thermal stresses during operating conditions, which may require periodic inspection of certain components. During operations of the turbomachinery 18, a fuel such as natural gas or syngas, may be routed to the turbomachinery 18 through one or more fuel nozzles 32 into a combustor 36. Air may enter the turbomachinery 18 through an air intake section 38 and may be compressed by a compressor 34. The compressor 34 may include a series of stages 40, 42, and 44 that compress the air. Each stage may include one or more sets of stationary vanes 46 and blades 48 that rotate to progressively increase the pressure to provide compressed air. The blades 48 may be attached to rotating wheels 50 connected to a shaft 52. The compressed discharge air from the compressor 34 may exit the compressor 34 through a diffuser section 56 and may be directed into the combustor 36 to mix with the fuel. For example, the fuel nozzles 32 may inject a fuel-air mixture into the combustor 36 in a suitable ratio for optimal combustion, emissions, fuel consumption, and power output. In certain embodiments, the turbomachinery 18 may include multiple combustors 36 disposed in an annular arrangement. Each combustor 36 may direct hot combustion gases into a turbine 54.

As depicted, the turbine 54 includes three separate stages 60, 62, and 64 surrounded by a casing 76. Each stage 60, 62, and 64 includes a set of blades or buckets 66 coupled to a respective rotor wheel 68, 70, and 72, which are attached to a shaft 74. As the hot combustion gases cause rotation of turbine blades 66, the shaft 74 rotates to drive the compressor 34 and any other suitable load, such as an electrical generator. Eventually, the turbomachinery 18 diffuses and exhausts the combustion gases through an exhaust section 80. Turbine components, such as the nozzles 32, intake 38, compressor 34, vanes 46, blades 48, wheels 50, shaft 52, diffuser 56, stages 60, 62, and 64, blades 66, shaft 74, casing 76, and exhaust 80, may use the disclosed embodiments, such as the NDT inspection devices 12, to inspect and maintain said components.

Additionally, or alternatively, the PTZ camera 16 may be disposed at various locations around or inside of the turbo machinery 18, and used to procure visual observations of these locations. The PTZ camera 16 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 16 may be additionally used to inspect the facilities 20, such as an oil and gas facility 20. Various equipment such as oil and gas equipment 84, may be inspected visually by using the borescope 14 and/or the PTZ camera 16. Advantageously, locations such as the interior of pipes or conduits 86, underwater (or underfluid) locations 88, and difficult to observe locations such as locations having curves or bends 90, may be visually inspected by using the mobile device 22 through the borescope 14 and/or PTZ camera 16. Accordingly, the mobile device operator 28 may more safely and efficiently inspect the equipment 18, 84 and locations 86, 88, and 90, and share observations in real-time or near real-time with location geographically distant from the inspection areas. It is to be understood that other NDT inspection devices 12 may be use the embodiments described herein, such as fiberscopes (e.g., articulating fiberscope, non-articulating fiberscope), and remotely operated vehicles (ROVs), including robotic pipe inspectors and robotic crawlers.

Figure 2:
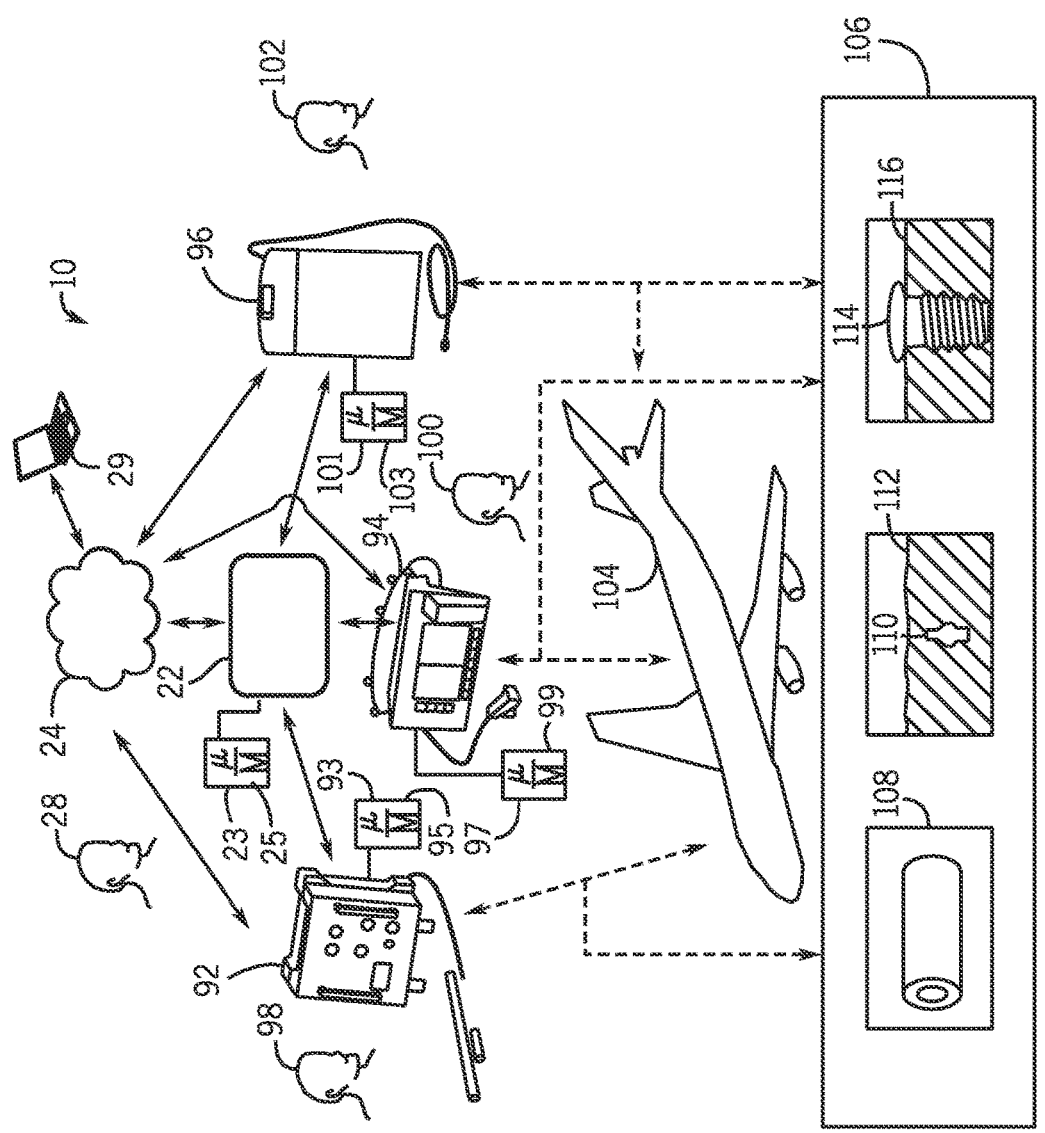
FIG. 2 is a block diagram illustrating further details of an embodiment of the distributed NDT system of FIG. 1.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 92, an ultrasonic inspection device, such as an ultrasonic flaw detector 94, and an x-ray inspection device, such a digital radiography device 96. The eddy current inspection device 92 may include one or more processors 93 and a memory 95. Likewise, the ultrasonic flaw detector 94 may include one or more processors 97 and a memory 104. Similarly, the digital radiography device 96 may include one or more processors 101 and a memory 103. In operations, the eddy current inspection device 92 may be operated by an eddy current operator 98, the ultrasonic flaw detector 94 may be operated by an ultrasonic device operator 100, and the digital radiography device 96 may be operated by a radiography operator 102.

As depicted, the eddy current inspection device 92, the ultrasonic flaw detector 94, and the digital radiography inspection device 96, may be communicatively coupled to the mobile device 22 by using wired or wireless conduits, including the conduits mentioned above with respect to FIG. 1. Additionally, or alternatively, the devices 92, 94, and 96 may be coupled to the mobile device 22 by using the cloud 24, for example the borescope 14 may be connected to a cellular "hotspot," and use the hotspot to connect to one or more experts in borescopic inspection and analsysis. Accordingly, the mobile device operator 28 may remotely control various aspects of operations of the devices 92, 94, and 96 by using the mobile device 22, and may collaborate with the operators 98, 100, and 102 through voice (e.g., voice over IP [VOIP]), data sharing (e.g., whiteboarding), providing data analytics, expert support and the like, as described in more detail herein.

Accordingly, it may be possible to enhance the visual observation of various equipment, such as an aircraft system 104 and facilities 106, with x-ray observation modalities, ultrasonic observation modalities, and/or eddy current observation modalities. For example, the interior and the walls of pipes 108 may be inspected for corrosion and/or erosion. Likewise, obstructions or undesired growth inside of the pipes 108 may be detected by using the devices 92, 94, and/or 96. Similarly, fissures or cracks 110 disposed inside of certain ferrous or non-ferrous material 112 may be observed. Additionally, the disposition and viability of parts 114 inserted inside of a component 116 may be verified. Indeed, by using the techniques described herein, improved inspection of equipment and components 104, 108, 112 and 116 may be provided. For example, the mobile device 22 may be used to interface with and provide remote control of the devices 14, 16, 92, 94, and 96.

Figure 3:
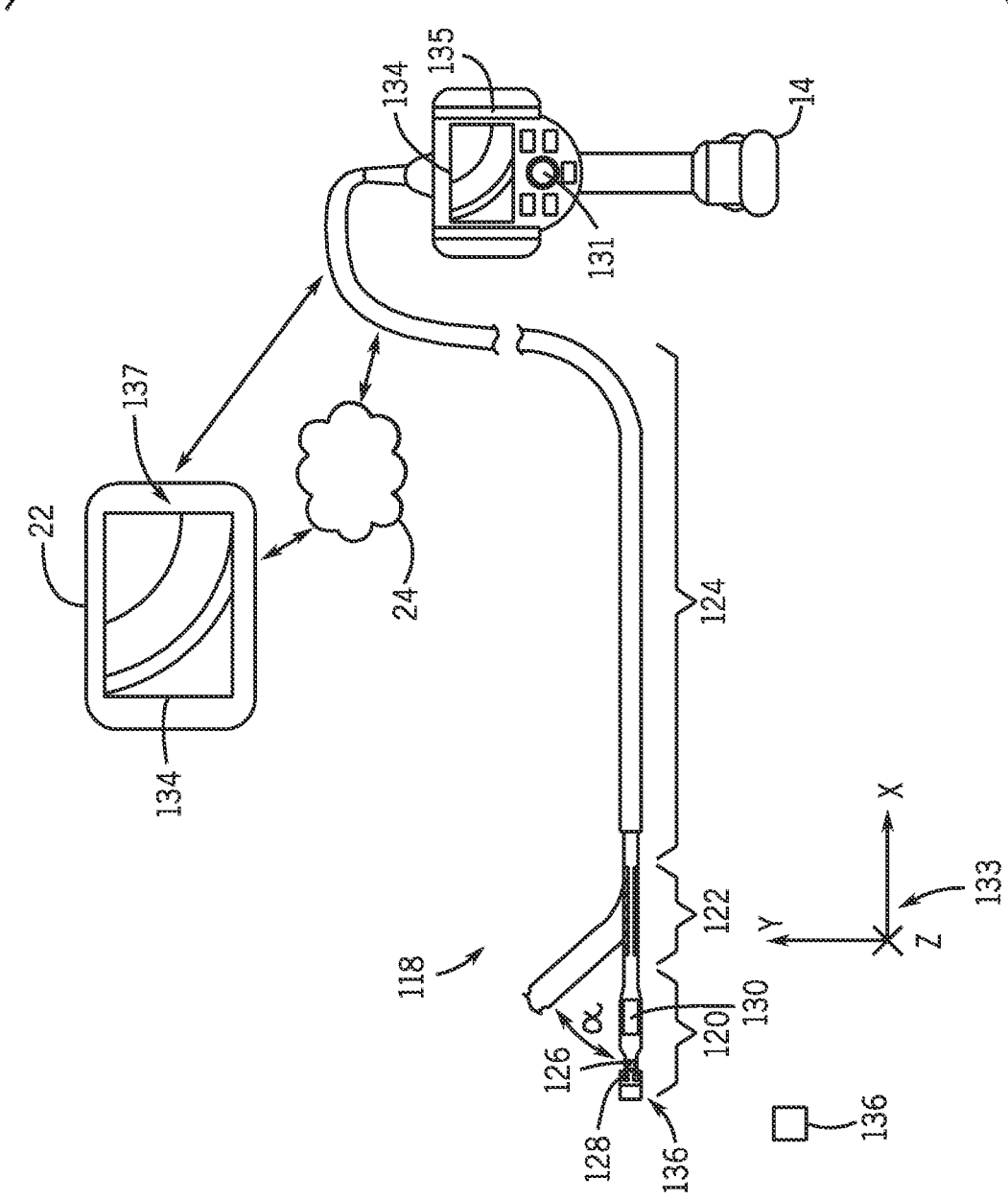
FIG. 3 is a front view illustrating an embodiment of a borescope system 14 communicatively coupled to the mobile device of FIG. 1 and a "cloud;"

FIG. 3 is a front view of the borescope 14 coupled to the mobile device 22 and the cloud 24. Accordingly, the borescope 14 may provide data to any number of devices connected to the cloud 24 or inside the cloud 24. As mentioned above, the mobile device 22 may be used to receive data from the borescope 14, to remote control the borescope 14, or a combination thereof. Indeed, the techniques described herein enable, for example, the communication of a variety of data from the borescope 14 to the mobile device 22, including but not limited to images, video, and sensor measurements, such as temperature, pressure, flow, clearance (e.g., measurement between a stationary component and a rotary component), and distance measurements. Likewise, the mobile device 22 may communicate control instructions, reprogramming instructions, configuration instructions, and the like, as described in more detail below.

As depicted the borescope 14, includes an insertion tube 118 suitable for insertion into a variety of location, such as inside of the turbomachinery 18, equipment 84, pipes or conduits 86, underwater locations 88, curves or bends 90, varies locations inside or outside of the aircraft system 104, the interior of pipe 108, and so on. The insertion tube 118 may include a head end section 120, an articulating section 122, and a conduit section 124. In the depicted embodiment, the head end section 120 may include a camera 126, one or more lights 128 (e.g., LEDs), and sensors 130. As mentioned above, the borescope's camera 126 may provide images and video suitable for inspection. The lights 128 may be used to provide for illumination when the head end 120 is disposed in locations having low light or no light.

During use, the articulating section 122 may be controlled, for example, by the mobile device 22 and/or a physical joy stick 131 disposed on the borescope 14. The articulating sections 122 may steer or "bend" in various dimensions. For example, the articulation section 122 may enable movement of the head end 120 in an X-Y plane X-Z plane and/or Y-Z plane of the depicted XYZ axes 133. Indeed, the physical joystick 131 and/or the mobile device 22 may both be used alone or in combination, to provide control actions suitable for disposing the head end 120 at a variety of angles, such as the depicted angle α. In this manner, the borescope head end 120 may be positioned to visually inspect desired locations. The camera 126 may then capture, for example, a video 134, which may be displayed in a screen 135 of the borescope 14 and a screen 137 of the mobile device 22, and may be recorded by the borescope 14 and/or the mobile device 22. In one embodiment, the screens 135 and 137 may be multi-touchscreens using capacitance techniques, resistive techniques, infrared grid techniques, and the like, to detect the touch of a stylus and/or one or more human fingers. Additionally or alternatively, images and the video 134 may be transmitted into the cloud 24.

Other data, including but not limited to sensor 130 data, may additionally be communicated and/or recorded by the borescope 14. The sensor 130 data may include temperature data, distance data, clearance data (e.g., distance between a rotating and a stationary component), flow data, and so on. In certain embodiments, the borescope 14 may include a plurality of replacement tips 136. For example, the replacement tips 136 may include retrieval tips such as snares, magnetic tips, gripper tips, and the like. The replacement tips 136 may additionally include cleaning and obstruction removal tools, such as wire brushes, wire cutters, and the like. The tips 136 may additionally include tips having differing optical characteristics, such as focal length, stereoscopic views, 3-dimensional (3D) phase views, shadow views, and so on. Additionally or alternatively, the head end 120 may include a removable and replaceable head end 120. Accordingly, a plurality of head ends 120 may be provided at a variety of diameters, and the insertion tube 118 maybe disposed in a number of locations having openings from approximately one millimeter to ten millimeters or more. Indeed, a wide variety of equipment and facilities may be inspected, and the data may be shared through the mobile device 22 and/or the cloud 24.

Figure 4:
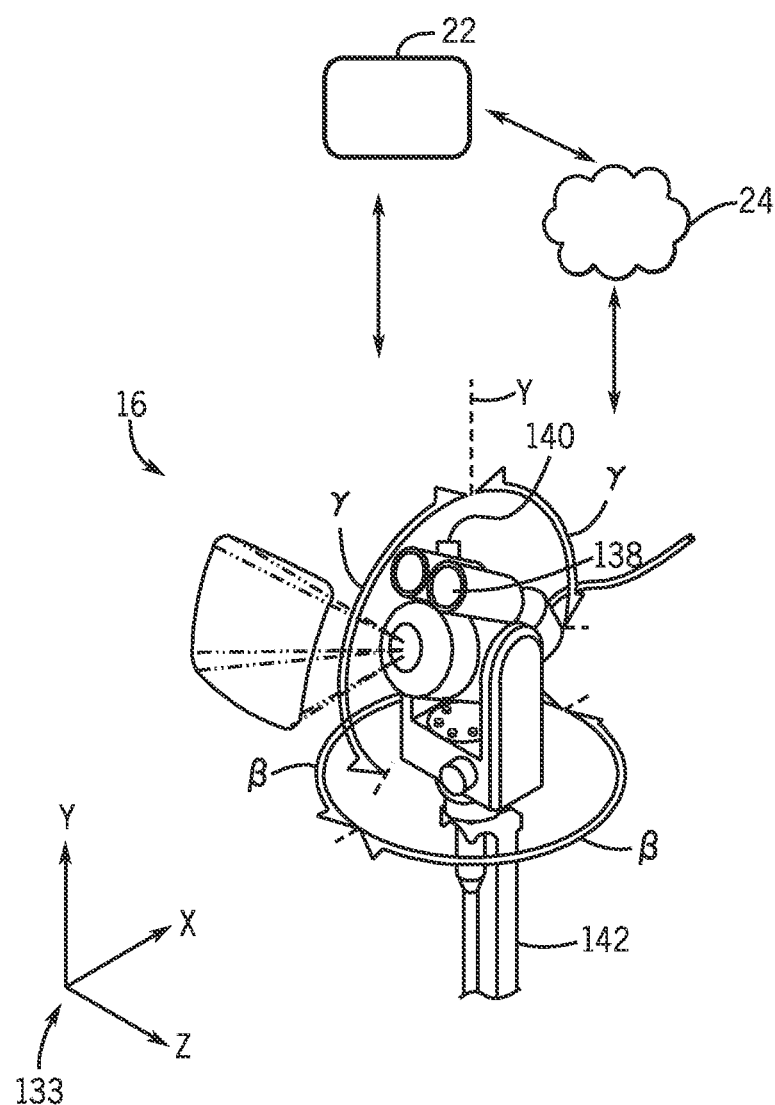
FIG. 4 is an illustration of an embodiment of a pan-tilt-zoom (PTZ) camera system communicatively coupled to the mobile device of FIG. 1.

FIG. 4 is a perspective view of an embodiment of the transportable PTZ camera 16 communicatively coupled to the mobile device 22 and to the cloud 24. As mentioned above, the mobile device 22 and/or the cloud 24 may remotely manipulate the PTZ camera 16 to position the PTZ camera 16 to view desired equipment and locations. In the depicted example, the PTZ camera 16 may be tilted and rotated about the Y-axis. For example, the PTZ camera 16 may be rotated at an angle β between approximately 0° to 180°, 0° to 270°, 0° to 360°, or more about the Y-axis. Likewise, the PTZ camera 16 may be tilted, for example, about the Y-X plane at an angle γ of approximately 0° to 100°, 0° to 120°, 0° to 150°, or more with respect to the Y-Axis. Lights 138 may be similarly controlled, for example, to active or deactivate, and to increase or decrease a level of illumination (e.g., lux) to a desired value. Sensors 140, such as a laser rangefinder, may also be mounted onto the PTZ camera 16, suitable for measuring distance to certain objects. Other sensors 140 may be used, including long-range temperature sensors (e.g., infrared temperature sensors), pressure sensors, flow sensors, clearance sensors, and so on.

The PTZ camera 16 may be transported to a desired location, for example, by using a shaft 142. The shaft 142 enables the camera operator 30 to move the camera and to position the camera, for example, inside of locations 86, 108, underwater 88, into hazardous (e.g., hazmat) locations, and so on. Additionally, the shaft 142 may be used to more permanently secure the PTZ camera 16 by mounting the shaft 142 onto a permanent or semi-permanent mount. In this manner, the PTZ camera 16 may be transported and/or secured at a desired location. The PTZ camera 16 may then transmit, for example by using wireless techniques, image data, video data, sensor 140 data, and the like, to the mobile device 22 and/or cloud 24. Accordingly, data received from the PTZ camera 16 may be remotely analyzed and used to determine the condition and suitability of operations for desired equipment and facilities. Indeed, the techniques described herein may provide for a comprehensive inspection and maintenance process suitable for planning, inspecting, analyzing, and/or sharing a variety of data by using the aforementioned devices 12, 14, 16, 22, 92, 94, 96, and the cloud 24, as described in more detail below with respect to FIG. 5.

Figure 5:
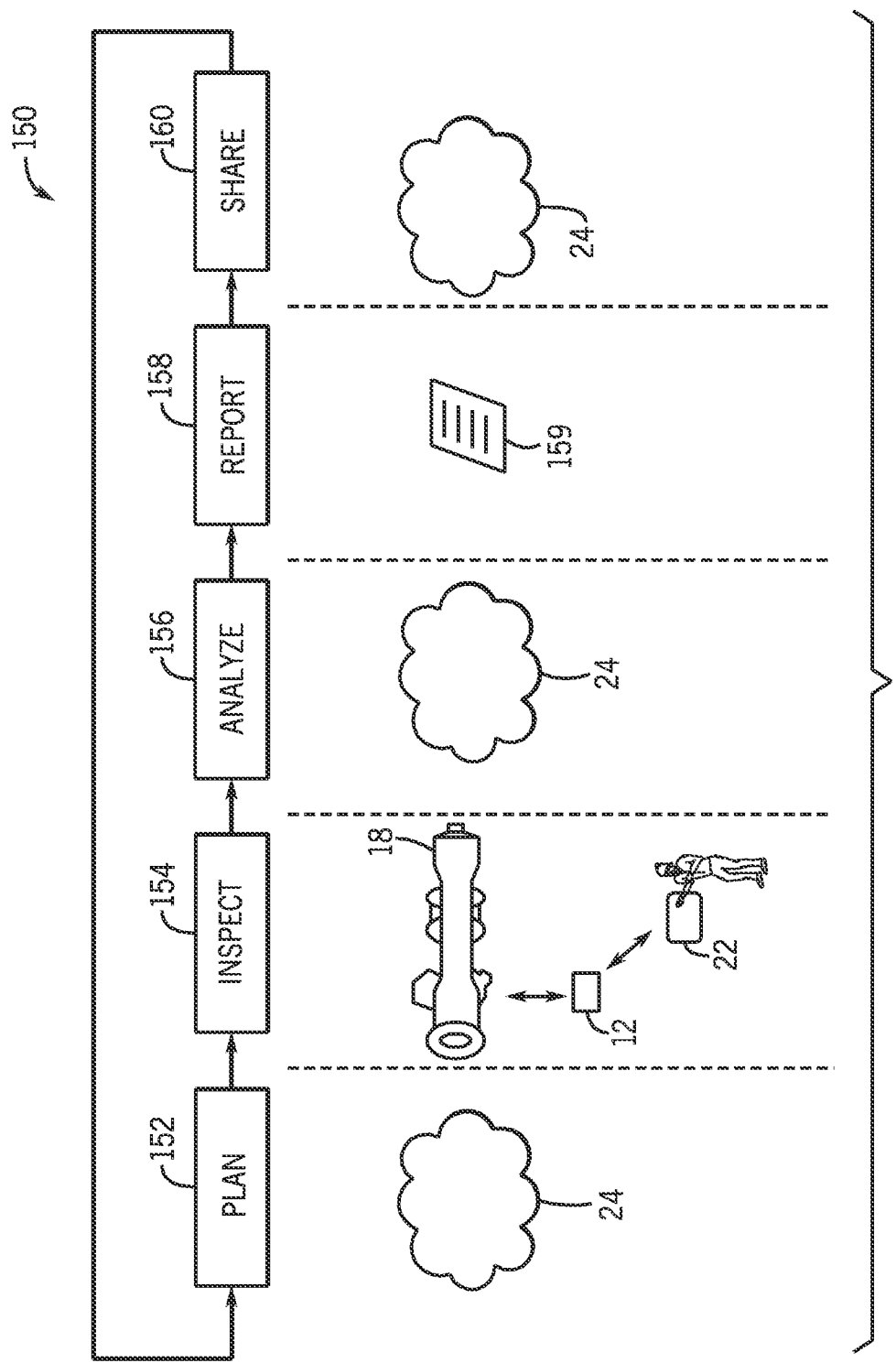
FIG. 5 is a flowchart illustrating an embodiment of a process useful in using the distributed NDT system for planning, inspecting, analyzing, reporting, and sharing of data, such as inspection data.

FIG. 5 is a flowchart of an embodiment of a process 150 suitable for planning, inspecting, analyzing, and/or sharing a variety of data by using the aforementioned devices 12, 14, 16, 22, 92, 94, 96, and the cloud 24. Indeed, the techniques described herein may use the devices 12, 14, 16, 22, 92, 94, 96 to enable processes, such as the depicted process 150, to more efficiently support and maintain a variety of equipment. In certain embodiments, the process 150 or portions of the process 150 may be included in non-transitory computer-readable media stored in memory, such as the memory 17, 21, 25, 95, 99, 103 and executable by one or more processors, such as the processors 15, 19, 23, 93, 97, 101.

In one example, the process 150 may plan (block 152) for inspection and maintenance activities. Data acquired by using the devices 12, 14, 16, 22, 42, 44, 46, an others, such as fleet data acquired from a fleet of turbomachinery 18, from equipment users (e.g., aircraft 104 service companies), and/or equipment manufacturers, may be used to plan (block 152) maintenance and inspection activities, more efficient inspection schedules for machinery, flag certain areas for a more detailed inspection, and so on. The process 150 may then enable the use of a single mode or a multi-modal inspection (block 154) of desired facilities and equipment (e.g., turbomachinery 18). As mentioned above, the inspection (block 154) may use any one or more of the NDT inspection devices 12 (e.g., borescope 14, PTZ camera 16, eddy current inspection device 92, ultrasonic flaw detector 94, digital radiography device 96), thus providing with one or more modes of inspection (e.g., visual, ultrasonic, eddy current, x-ray). In the depicted embodiment, the mobile device 22 may be used to remote control the NDT inspection devices 12, to analyze data communicated by the NDT inspection devices 12, to provide for additional functionality not included in the NDT inspection devices 12 as described in more detail herein, to record data from the NDT inspection devices 12, and to guide the inspection (block 154), for example, by using menu-driven inspection (MDI) techniques, among others.

Results of the inspection (block 154), may then be analyzed (block 156), for example, by using the NDT device 12, by transmitting inspection data to the cloud 24, by using the mobile device 22, or a combination thereof. The analysis may include engineering analysis useful in determining remaining life for the facilities and/or equipment, wear and tear, corrosion, erosion, and so forth. The analysis may additionally include operations research (OR) analysis used to provide for more efficient parts replacement schedules, maintenance schedules, equipment utilization schedules, personnel usage schedules, new inspection schedules, and so on. The analysis (block 156) may then be reported (block 158), resulting in one or more reports 159, including reports created in or by using the cloud 24, detailing the inspection and analysis performed and results obtained. The reports 159 may then be shared (block 160), for example, by using the cloud 24, the mobile device 22, and other techniques, such as workflow sharing techniques. In one embodiment, the process 150 may be iterative, thus, the process 150 may iterate back to planning (block 152) after the sharing (block 160) of the reports 159. By providing for embodiments useful in using the devices (e.g., 12, 14, 16, 22, 92, 94, 96) described herein to plan, inspect, analyze, report, and share data, the techniques described herein may enable a more efficient inspection and maintenance of the facilities 20, 106 and the equipment 18, 104. Indeed, the transfer of multiple categories of data may be provided, as described in more detail below with respect to FIG. 6.

Figure 6:
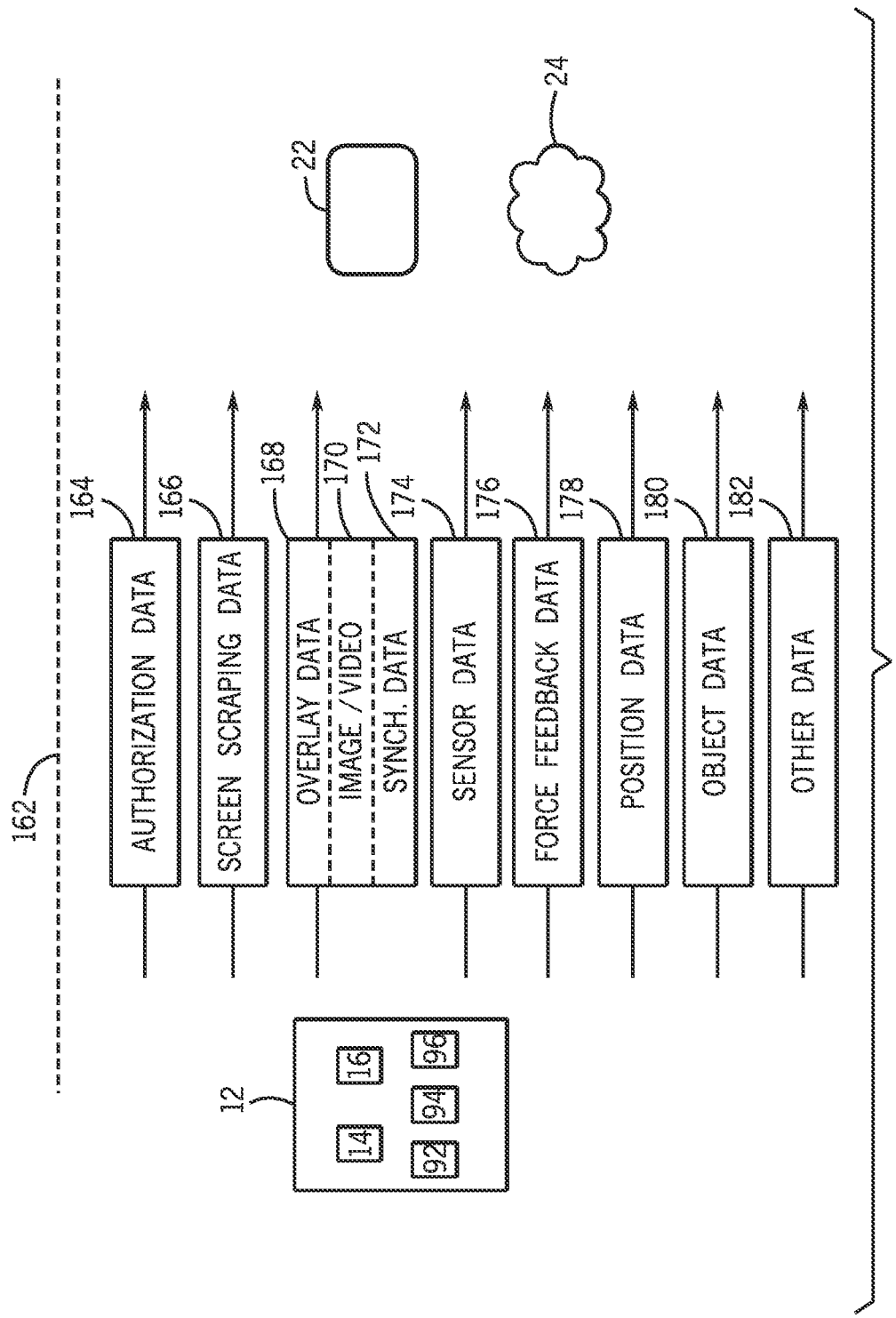
FIG. 6 is a block diagram of an embodiment of information flow through a wireless conduit.

FIG. 6 is a data flow diagram depicting an embodiment of the flow of various data categories originating from the NDT inspection devices 12 (e.g., devices 14, 16, 92, 94, 96) and transmitted to the mobile device 22 and/or the cloud 24. As mentioned above, the NDT inspection devices 12 may use a wireless conduit 162 to transmit the data. In one embodiment, the wireless conduit 112 may include WiFi (e.g., 802.11X), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. Accordingly, an authorization data 164 may be used to provide any number of authorization or login information suitable to pair or otherwise authenticate the NDT inspection device 12 to the mobile device 22 and/or the cloud 24. Additionally, the wireless conduit 162 may dynamically compress data, depending on, for example, currently available bandwidth and latency. The mobile device 22 may then uncompress and display the data. Compression/decompression techniques may include H.261, H.263, H.264, moving picture experts group (MPEG), MPEG-1, MPEG-2, MPEG-3, MPEG-4, DivX, and so on.

In certain modalities (e.g., visual modalities), images and video may be communicated by using certain of the NDT inspection devices 12. Other modalities may also send video, sensor data, and so on, related to or included in their respective screens. The NDT inspection device 12 may, in addition to capturing images, overlay certain data onto the image, resulting in a more informative view. For example, a borescope tip map may be overlaid on the video, showing an approximation of the disposition of a borescope tip during insertion so as to guide the operator 26 to more accurately position the borescope camera 126. The overlay tip map may include a grid having four quadrants, and the tip 136 disposition may be displayed as dot in any portion or position inside of the four quadrants. A variety of overlays may be provided, as described in more detail below, including measurement overlays, menu overlays, annotation overlays, and object identification overlays. The image and video data, such as the video 84, may then be displayed, with the overlays generally displayed on top of the image and video data.

In one embodiment, the overlays, image, and video data may be "screen scraped" from the screen 135 and communicated as screen scrapping data 166. The screen scrapping data 166 may then be displayed on the mobile device 22 and other display devices communicatively coupled to the cloud 24. Advantageously, the screen scrapping data 166 may be more easily displayed. Indeed, because pixels may include both the image or video and overlays in the same frame, the mobile device 22 may simply display the aforementioned pixels. However, providing the screen scraping data may merge both the images with the overlays, and it may be beneficial to separate the two (or more) data streams. For example, the separate data streams (e.g., image or video stream, overlay stream) may be transmitted approximately simultaneously, thus providing for faster data communications. Additionally, the data streams may be analyzed separately, thus improving data inspection and analysis.

Accordingly, in one embodiment, the image data and overlays may be separated into two or more data streams 168 and 170. The data stream 168 may include only overlays, while the data stream 170 may include images or video. In one embodiment, the images or video 170 may be synchronized with the overlays 168 by using a synchronization signal 172. For example, the synchronization signal may include timing data suitable to match a frame of the data stream 170 with one or more data items included in the overlay stream 168. In yet another embodiment, no synchronization data 172 data may be used. Instead, each frame or image 170 may include a unique ID, and this unique ID may be matched to one or more of the overlay data 168 and used to display the overlay data 168 and the image data 170 together.

The overlay data 168 may include a tip map overlay. For example, a grid having four squares (e.g., quadrant grid) may be displayed, along with a dot or circle representing a tip 136 position. This tip map may thus represent how the tip 136 is being inserted inside of an object. A first quadrant (top right) may represent the tip 136 being inserted into a top right corner looking down axially into the object, a second quadrant (top left) may represent the tip 136 being inserted into a left right corner looking down axially, a third quadrant (bottom left) may represent the tip 136 being inserted into a bottom left corner, and a fourth quadrant (bottom right) may represent the tip 136 being inserted into a bottom right corner. Accordingly, the borescope operator 26 may more easily guide insertion of the tip 136.

The overlay data 168 may also include measurement overlays. For example, measurement such as length, point to line, depth, area, multi-segment line, distance, skew, and circle gauge may be provided by enabling the user to overlay one or more cursor crosses (e.g., "+") on top of an image. In one embodiment a stereo probe measurement tip 136, or a shadow probe measurement tip 136 may be provided, suitable for measurements inside of objects, including stereoscopic measurements and/or by projecting a shadow onto an object. By placing a plurality of cursor icons (e.g., cursor crosses) over an image, the measurements may be derived using stereoscopic techniques. For example, placing two cursors icons may provide for a linear point-to-point measurement (e.g., length). Placing three cursor icons may provide for a perpendicular distance from a point to a line (e.g., point to line). Placing four cursor icons may provide for a perpendicular distance between a surface (derived by using three cursors) and a point (the fourth cursor) above or below the surface (e.g., depth). Placing three or more cursors around a feature or defect may then give an approximate area of the surface contained inside the cursors. Placing three or more cursors may also enable a length of a multi-segment line following each cursor.

Likewise, by projecting a shadow, the measurements may be derived based on illumination and resulting shadows. Accordingly, by positioning the shadow across the measurement area, then placing two cursors as close as possible to the shadow at furthermost points of a desired measurement may result in the derivation of the distance between the points. Placing the shadow across the measurement area, and then placing cursors at edges (e.g., illuminated edges) of the desired measurement area approximately to the center of a horizontal shadow may result in a skew measurement, otherwise defined as a linear (point-to-point) measurement on a surface that is not perpendicular to the probe 14 view. This may be useful when a vertical shadow is not obtainable.

Similarly, positioning a shadow across the measurement area, and then placing one cursor on a raised surface and a second cursor on a recessed surface may result in the derivation of depth, or a distance between a surface and a point above or below the surface. Positioning the shadow near the measurement area, and then placing a circle (e.g., circle cursor of user selectable diameter, also referred to as circle gauge) close to the shadow and over a defect may then derive the approximate diameter, circumference, and/or area of the defect.

Overlay data 168 may also include annotation data. For example, text and graphics (e.g. arrow pointers, crosses, geometric shapes) may be overlaid on top of an image to annotate certain features, such as "surface crack." Additionally, audio may be captured by the NDT inspection device 12, and provided as an audio overlay. For example, a voice annotation, sounds of the equipment undergoing inspection, and so on, may be overlaid on an image or video as audio. The overlay data 168 received by the mobile device 22 and/or cloud 24 may then be rendered by a variety of techniques. For example, HTML5 or other markup languages may be used to display the overlay data 168. In one embodiment, the mobile device 22 and/or cloud 24 may provide for a first user interface different from a second user interface provided by the NDT device 12. Accordingly, the overlay data 168 may be simplified and only send basic information. For example, in the case of the tip map, the overlay data 168 may simply include X and Y data correlative to the location of the tip, and the first user interface may then use the X and Y data to visually display the tip on a grid.

Additionally sensor data 174 may be communicated. For example, data from the sensors 126, 140, and x-ray sensor data, eddy current sensor data, and the like may be communicated. In certain embodiments, the sensor data 174 may be synchronized with the overlay data 168, for example, overlay tip maps may be displayed alongside with temperature information, pressure information, flow information, clearance, and so on. Likewise, the sensor data 174 may be displayed alongside the image or video data 170.

In certain embodiments, force feedback or haptic feedback data 176 may be communicated. The force feedback data 176 may include, for example, data related to the borescope 14 tip 136 abutting or contacting against a structure, vibrations felt by the tip 136 or vibration sensors 126, force related to flows, temperatures, clearances, pressures, and the like. The mobile device 22 may include, for example, a tactile layer having fluid-filled microchannels, which, based on the force feedback data 176, may alter fluid pressure and/or redirect fluid in response. Indeed, the techniques describe herein, may provide for responses actuated by the mobile device 22 suitable for representing sensor data 174 and other data in the conduit 162 as tactile forces.

The NDT devices 12 may additionally communicate position data 178. For example, the position data 178 may include locations of the NDT devices 12 in relation to equipment 18, 104, and/or facilities 20, 106. For example, techniques such as indoor GPS, RFID, triangulation (e.g., WiFi triangulation, radio triangulation) may be used to determine the position 178 of the devices 12. Object data 180 may include data related to the object under inspection. For example, the object data 180 may include identifying information (e.g., serial numbers), observations on equipment condition, annotations (textual annotations, voice annotations), and so on. Other types of data 182 may be used, including but not limited to menu-driven inspection data, which when used, provides a set of pre-defined "tags" that can be applied as text annotations and metadata. These tags may include location information (e.g., 1st stage HP compressor) or indications (e.g., foreign object damage) related to the object undergoing inspection. Other data 182 may additionally include remote file system data, in which the mobile device 22 may view and manipulate files and file constructs (e.g., folders, subfolders) of data located in the memory 25 of the NDT inspection device 12. Accordingly, files may be transferred to the mobile device 22 and cloud 24, edited and transferred back into the memory 25. By communicating the data 164-182 to the mobile device 22 and the cloud 24, the techniques described herein may enable a faster and more efficient process 150.

Figure 7:
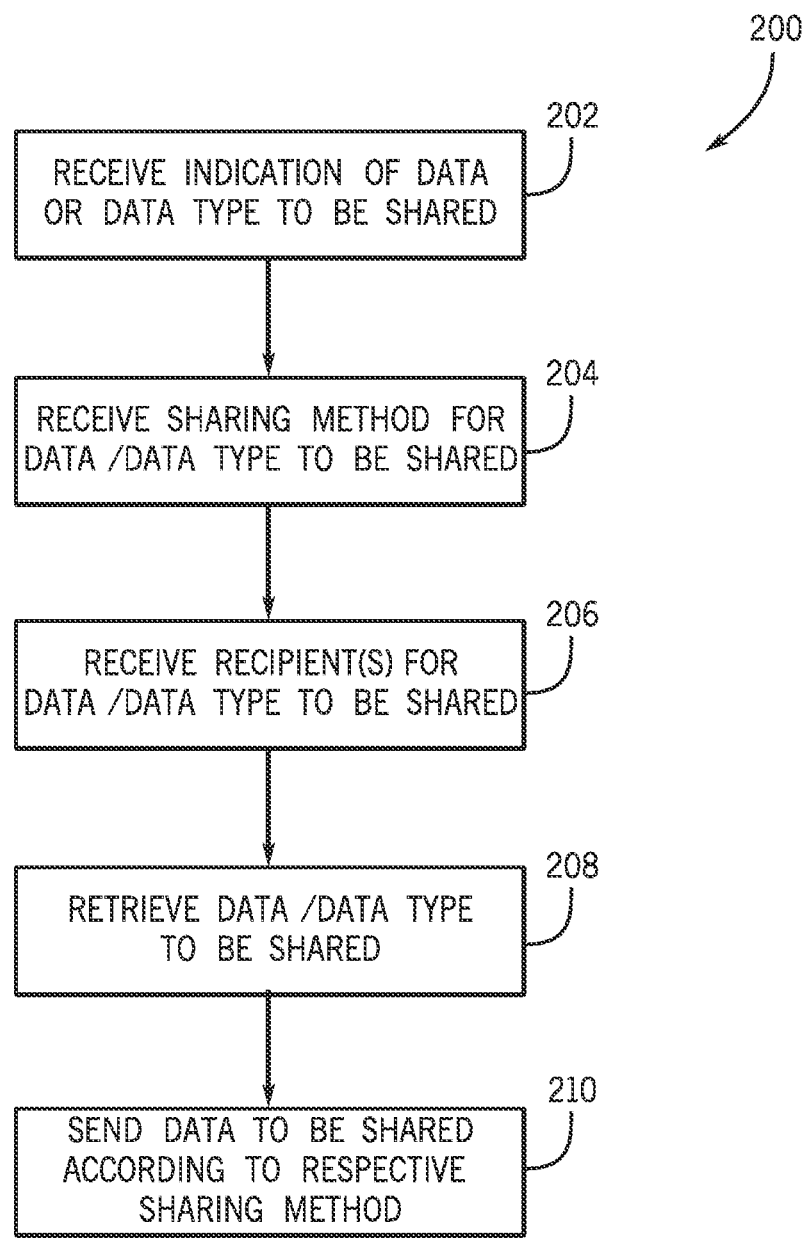
FIG. 7 is a flowchart of an embodiment of a process for sharing data that corresponds to the NDT system of FIG. 1, in accordance with aspects of the present disclosure.

Keeping the foregoing in mind, FIG. 7 illustrates an embodiment of a process 200 for sharing data that corresponds to the NDT system 10, such as the data depicted above with respect to FIG. 6. In certain embodiments, the process 200 or portions of the process 200 may be included in non-transitory computer-readable media stored in memory, such as the memory 15, 19, 23, 25, 93, 97, 101 and executable by one or more processors, such as the processors 17, 21, 25, 95, 99, 103 and the cloud 24.

In one embodiment, an application containing computer instructions executable by the mobile device 22, the NDT inspection devices 12, and/or the cloud 24 may be used to collect data that may be related to the inspection of a piece of equipment (e.g., devices 12, 14, 16, 22, 42, 44, 46) within the NDT system 10 or may be used to generate reports 159 related to the NDT system 10. Although the process 200 depicts a particular order in which the process 200 may be performed, it should be noted that the process 200 may also be performed in a different order.

At block 202, the application may receive an indication of data or a type of data that the mobile device operator 28 may designate as data or a type of data that will be shared. That is, the mobile device operator 28 may select data or a type of data that will be shared as it becomes available or is generated by the application. In certain embodiments, the data or type of data may be related to an inspection 154 of some non-destructive testing results of a piece of equipment. In certain embodiments, the indication of data or the type of data to be shared may be embedded as part of a configuration for the application. That is, the data or type of data to be shared may be pre-designated according to a workflow associated with the respective inspection of the piece of equipment. As such, the workflow and the application configuration may be established and stored in a server or like device.

In addition to receiving the data or data that corresponds to the type of data to be shared (e.g., data provided through conduit 162), the application, at block 204, may receive a sharing process or a format in which the data or type of data will be shared. The format in which data may be shared may include, for example, sending an electronic-mail (e-mail) message, text message, report 159, or the like that describes or includes the data that is designated to be shared to one or more recipients. Along with the sharing process or format, the application may receive an indication of a template that may be used to present the data. In this case, prior to sending the data, the application may apply the template, generate a report using the template, and send the report. The template and the use of the template may be embedded as part of the configuration for the application or pre-designated according to the workflow as discussed above.

In certain embodiments, the application may upload the data to be shared into the cloud 24 such that other individuals may download the data. Additionally, along with uploading the data or data that corresponds to the type of data to be shared, the application may send a message to various individuals, who may be interested in the uploaded data, indicating that the data has been uploaded.

At block 206, the application may receive one or more recipients for the data to be shared. In certain embodiments, the NDT operator 28, 26, 30, 98, 100, and/or 102 may specify one or more recipients for each data and/or type of data received at block 202. The recipients may include experts or management personnel that may correspond to the data or type of data, third party entities (e.g., maintenance service providers, manufacturers), regulatory entities (e.g., Federal Aviation Administration [FAA], Environmental Protection Agency [EPA], Department of Transportation [DOT]), federal and state entities, and so on. In certain embodiments, the application may present a list of potential recipients on a display based on the data or type of data being shared. Additional details with regard to how the application presents this list will be described below with reference to FIG. 8.

After receiving the recipients for each data or type of data, at block 208, the application may retrieve the data that may correspond to the data specified at block 202 from its memory, such as memory 25. In one embodiment, the application may retrieve the data as the data is being generated. That is, the application may automatically retrieve data that is to be shared once the data has been saved in a memory, in approximately real-time or near real-time.

At block 210, the application may send the data designated to be shared at block 202 to respective recipient(s). The data may be sent according to the sharing method or format specified at block 204. As such, the application may modify or alter the data retrieved at block 208 and send the modified data to the recipients received at block 206.

In certain embodiments, each recipient may have a preferred format to receive shared data. As such, when receiving the recipients at block 206, the application may also receive a preferred process or format in which each recipient may receive data. In this case, the application may send the data designated to be shared at block 202 to respective recipient(s) in a format that corresponds to the preferred method in which each respective recipient may specify to receive data. That is, the application may override or disregard the sharing method received at block 204 and send the data as per the preferred method of the respective recipient.

Figure 8:
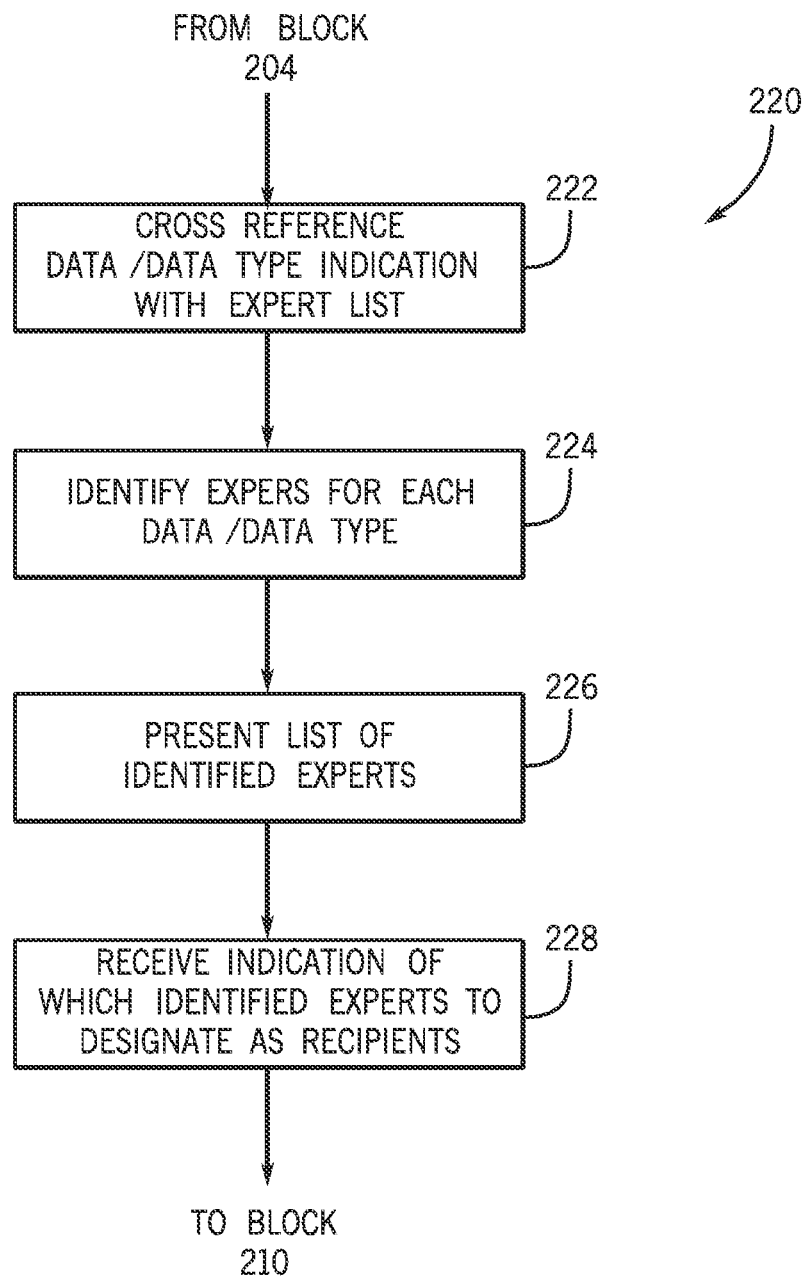
FIG. 8 is a flowchart of an embodiment of a process for presenting a list of recipients for shared data that corresponds to the NDT system of FIG. 1, in accordance with aspects of the present disclosure.

As mentioned above, at block 206, the application may present a list of potential recipients on a display according to a process 220 depicted in FIG. 8. That is, the method 220 may provide additional details with regard to how the application may receive recipients for the data to be shared. For example, at block 222, the application may cross reference the data or type of data indicated to be shared at block 202 with a list of individuals who may be associated with the NDT system 10. The list of individuals may include one or more individuals or groups of individuals that may have relevant expertise in one or more areas of non-destructive testing procedures, techniques, results, or the like. Moreover, the list of individuals may also chronicle each individual's experience and knowledge with various types of equipment. Entities may also be listed, such as third party entities (e.g., maintenance service providers, manufacturers), regulatory entities (e.g., Federal Aviation Administration [FAA], Environmental Protection Agency [EPA], Department of Transportation [DOT]), federal and state entities, and so on. The list of individuals may be received separately from a server via the cloud 24 based on a database that may include a mapping of the data, the data type, the application, the application type, and the like and list of individuals.

In one embodiment, the application may associate the data received at block 202 with a problem or issue that corresponds to the equipment associated with the data. For example, if the data received at block 202 is related to a crack within the airframe of an aircraft 104, the application may associate the data with a problem related to the structural integrity of the airframe or the like. Here, the application may determine that the problem may be associated or related to a group of individuals and/or entities. As such, the application may send the data to the group of individuals and/or entities who may be able to better assess the problem and assist the NDT operator in solving the problem.

At block 224, the application may identify individuals for each piece of data based on the cross-reference results of block 222. That is, for each piece of data, the application may identify one or more individuals or entities that may have relevant expertise with regard to the individual piece of data. Alternatively, for each piece of data, the application may identify one or more individuals or entities that may have relevant expertise with regard to tagged or identified problems (e.g., defects or defect types).

After identifying the individuals, at block 226, the application may present a list of individuals related to a selected piece of data or type of data on a display. As such, the NDT operator may have the opportunity to view and select one or more individuals to which he may send the selected data. In certain embodiments, the list of individuals may be ranked according to the individual's relevant expertise with regard to the selected data. Additionally or alternatively, the list of individuals may include details regarding each individual's expertise and various other characteristics regarding the individual. For example, each individual's entry may include a biography or resume detailing his/her expertise, which may include number of years in the relevant industry, equipment familiarity levels, association with pre-designated group of individuals for a particular technology, and the like. Entity entries may include contact personnel, areas of expertise, cost data (e.g., service cost data, manufacturing cost data), and so on. In one embodiment, each individual's and/or entity's entry may also include a preferred method for communication (e.g., e-mail, text message) and details (e.g., e-mail address, telephone number, contact information)

regarding the preferred method for communication for each respective individual and/or entity.

In another embodiment, the list of individuals or entities may be organized based on an organizational structure. For example, a senior inspector may be presented higher on the list as compared to a new inspector. The list of individuals or entities may also be organized based on original equipment manufacturers (OEMs) of the asset being inspected. As such, the OEMs may receive information related to problems or inspection results that may be associated with their manufactured parts. Moreover, the list of individuals or entities may be organized based on a creator of an application being executed by the mobile device 22, the NDT inspection device 12, or the like. That is, the creator of the application being used in the mobile device 22 may wish to receive certain indications related to the shared data or the shared data, itself.

At block 228, the application may receive an indication or input that may designate one or more individuals or entities in the list of individuals or entities as recipients. That is, the NDT operator 26, 28, 30, 98, 100, and/or 102 may provide input to the application that indicates which individuals and entities should be recipients to receive the selected data. After receiving the selection of individuals and/or entities, the application may proceed to block 210 of FIG. 7 and send the selected data to the selected individuals. Prior to sending the data, the application may apply a report template or the like to the selected data such that the selected data may be presented in a more readable or user-friendly manner. Moreover, upon receiving the shared data, the recipient may pass comments and flag the data as rejected or accepted and the data may then be returned to the inspector performing the inspection, thereby reducing workflow time.

Figure 9:
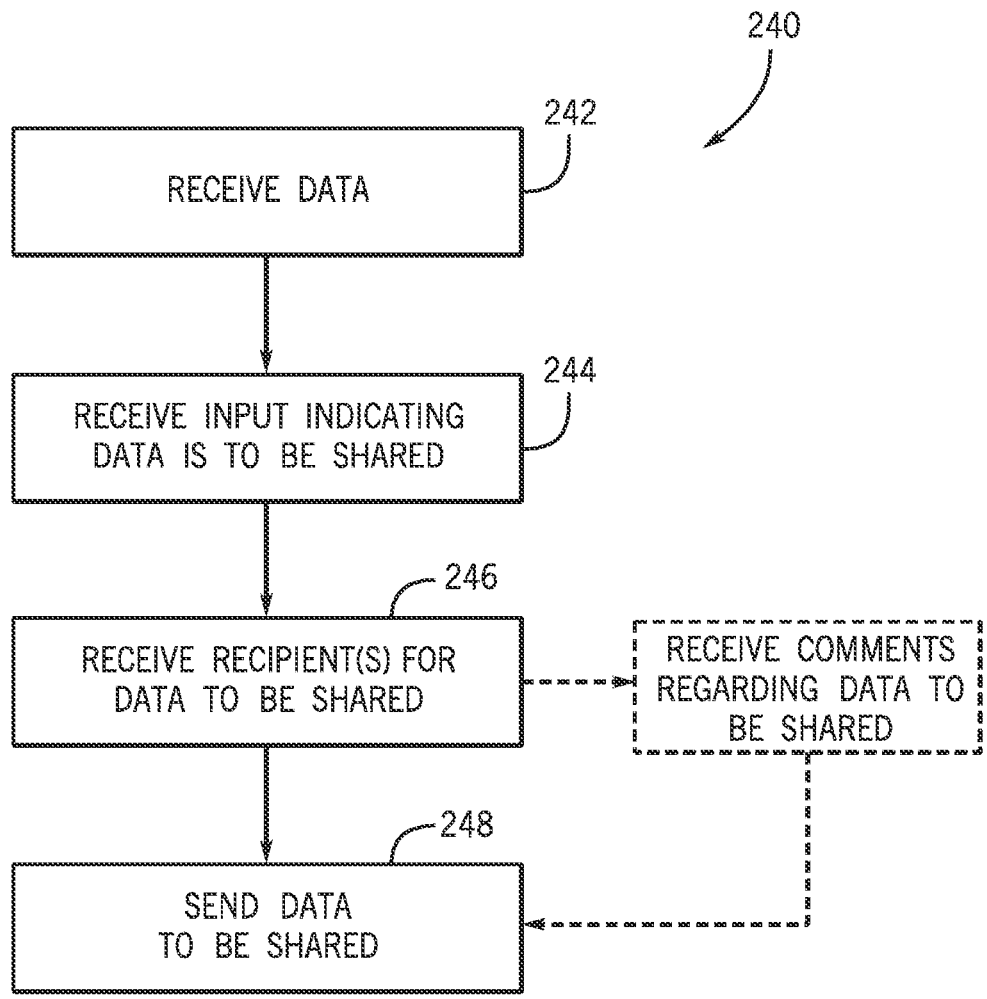
FIG. 9 is a flowchart of an embodiment of a process for sharing data that corresponds to the NDT system of FIG. 1 in real time or near real time, in accordance with aspects of the present disclosure.

In certain embodiments, the NDT operator 26, 28, 30, 98, 100, and/or 102 may observe or acquire data related to the NDT system 10 that may not be previously designated as data to be shared. As such, the NDT operator 26, 28, 30, 98, 100, and/or 102 may wish to designate data to be shared in real time soon after the data has been acquired or stored in an inspection report or the like. Keeping this in mind, FIG. 9 depicts a process 240 for sharing data related to the NDT system in real time or near real time. Although the process 240 depicts a particular order in which the process 240 may be performed, it should be noted that the process 240 may also be performed in a different order. In certain embodiments, the process 240 or portions of the process 240 may be included in non-transitory computer-readable media stored in memory, such as the memory 15, 19, 23, 25, 93, 97, 101 and executable by one or more processors, such as the processors 17, 21, 25, 95, 99, 103 and the cloud 24.

At block 242, the application may receive data related to equipment in the NDT system 10. For instance, the application may receive results of an eddy current test on the aircraft 104 frame that indicates that a crack may exist within the airframe. If the data that corresponds to the results of the eddy current test was not previously designated as data that will be shared, the application may provide an option to the NDT operator 26, 28, 30, 98, 100, and/or 102 to designate the data to be shared, for example in real-time or near real-time.

As such, at block 244, the application may receive an input indicating that the data received at block 242 is to be shared with certain NDT personnel. In one embodiment, the application may receive an input at an icon or image depicted on a graphical user interface (GUI) via an input device (e.g., pointing device, keyboard) on the mobile device 22 such that the input may designate the data to be shared.

At block 246, the application may receive one or more recipients designated to receive the data associated with the input described above with regard to block 244. After receiving the input at block 244, the application may present a list of potential recipients on a display. In addition to receiving the recipients, the application may receive a sharing method as described above with reference to block 204 of FIG. 7. In certain embodiments, the application may present a list of potential recipients using a similar process described above with reference to block 206 of FIG. 7.

After receiving the recipients, at block 248, the application may send the data associated with the input of block 244 to the recipients specified at block 246. In one embodiment, the application may send the data as soon as the recipients have been received at block 246. However, in some embodiments, the application may also send the data using a burst transmission. That is, the application may wait to send the data when an connectivity signal (e.g., Internet) becomes available. As a result, the process 240 provides a way to designate data to be shared without pre-designating the data as being shared.

In certain embodiments, after receiving the recipients associated with the data to be shared, at block 250, the application may receive comments regarding the data to be shared. For instance, if the received data of block 242 is a screen view of a display (e.g., display 135), the application may receive drawings or text or any other data (e.g., data communicated via conduit 162) on the screen view from the NDT operator 26, 28, 30, 98, 100, and/or 102 to indicate his comments, questions, or concerns with the data depicted in the screen view (e.g., annotated overlays 168). In this manner, the recipient may better understand the context of the data and provide advice to the NDT operator 26, 28, 30, 98, 100, and/or 102 accordingly. After receiving the comments, the application may, at block 248, send the data with the corresponding comments to the recipient received at block 246.

Figure 10:
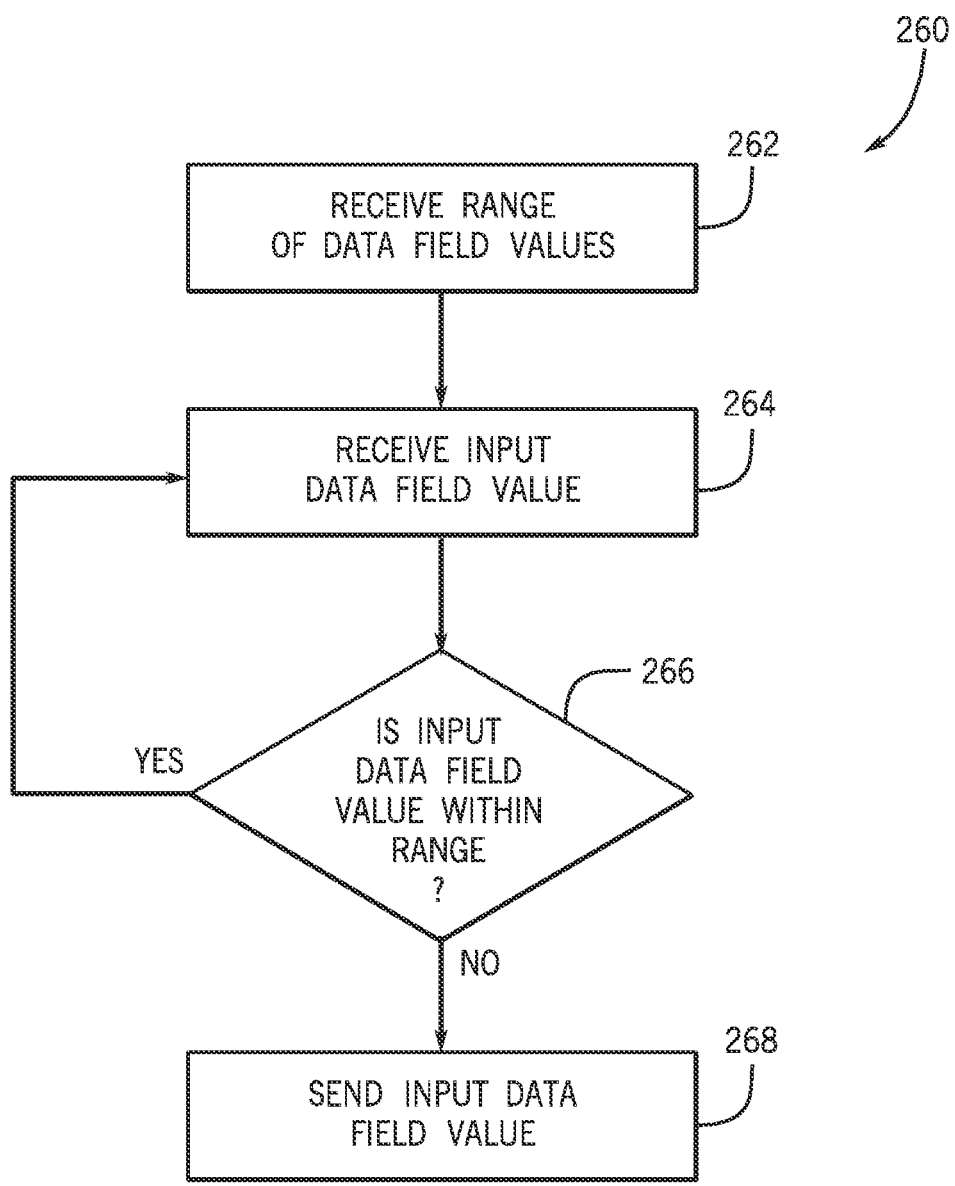
FIG. 10 is a flowchart of an embodiment of a process for automatically sharing data that corresponds to the NDT system of FIG. 1, in accordance with aspects of the present disclosure.

Keeping the foregoing in mind, the application may also employ a process 260 for automatically sharing data acquired from the NDT system 10, as shown in FIG. 10. Referring now to FIG. 10, at block 262, the application may receive one or more ranges of data field values for one or more data fields in the application. For instance, the rage of data field values may correspond to a range of expected values for the corresponding data field. The range of expected values may be determine based on empirical or historical data related to the data field or based on simulated results for the corresponding data field.

At block 264, the application may receive an input data field value for a respective data field. That is, the NDT operator 26, 28, 30, 98, 100, and/or 102 may perform a test or inspection on a piece of equipment in the NDT system 10 and enter a reading or measurement in the respective data field.

At block 266, the application may determine whether the input data field value is within a respective range of data field values received at block 262. If the input data field value is within the respective range of data field values, the application may return to block 264 and continue receiving input data field values.

If, however, the input data field value is not within the respective range of data field values, the application may proceed to block 268. At block 268, the application may send the input data field value to one or more recipients who may be designated as individuals or associated with the input data field value as described above. In certain embodiments, in addition to the input data field value, the application may send information with regard to the context of the input data field value. For example, the application may send information related to a type of report in which the input data field value may exist, an expected range of values for the input data field value, date and time information related to when the input data field value was received, and any other information that may provide context for the input data field value such that the recipient may properly analyze the input data field value.

In certain embodiments, the input data field value received at block 264 may not correspond to a data field that has a range of data field values associated therewith. In this case, the NDT operator 26, 28, 30, 98, 100, and/or 102 may specify to the application whether the application may automatically send the input data field value or may not send the input data field value.

Figure 11:
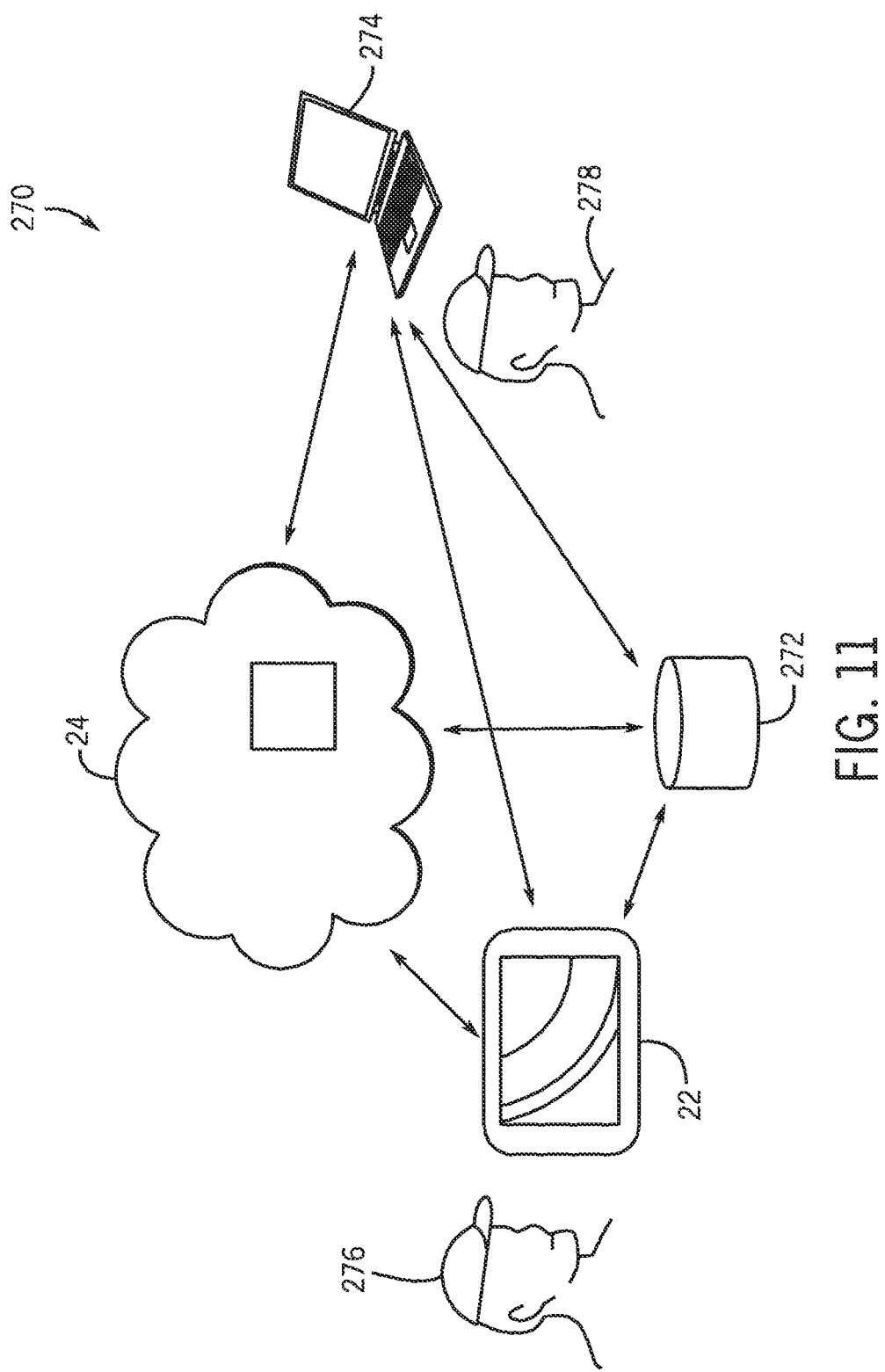
FIG. 11 is a block diagram of a collaboration system that corresponds to the NDT system of FIG. 1, in accordance with aspects of the present disclosure.

In addition to providing techniques for sharing NDT data, in certain embodiments, the NDT system 10 may provide a computing environment such that the NDT operators may collaborate with each other. For example, FIG. 11 depicts a block diagram of a collaboration system 270 that may provide a computing environment for NDT operators, experts on NDT inspection devices 12, experts on assets being inspected, and the like to collaborate with each other with regard to various aspects of the NDT system 10. To create this collaborative computing environment, the collaboration system 270 may include the mobile device 22, a database 272, and a client-computing device 274. The client-computing device 274 may include for example, a tablet, a cell phone (e.g., smart phone), a notebook, a laptop, a desktop, or any other computing device. In one embodiment, the mobile device 22, the database 272, and the client-computing device 274 may directly communicate or exchange information with each other or communicate with each other via the cloud 24.

Generally, an NDT inspector 276 (e.g., operator 26, 28, 30, 48, 50, 52) may use the mobile device 22 to perform various types of analysis and monitoring operations on equipment in the NDT system 10. As such, the NDT inspector 276 may enter data that corresponds to the equipment (e.g., devices 12, 14, 16, 22, 42, 44, 46) in the NDT system 10 into an application via the mobile device 22. In certain embodiments, the application may analyze or record the data that corresponds to the equipment in the NDT system 10.

While the NDT inspector 276 collects data, the NDT inspector 276 may enter data or encounter a situation in which he may want to collaborate with a remote NDT inspector 278. In this case, the NDT inspector 276 may use the NDT collaboration system 270 to initiate a field request for support from the NDT inspector 278. That is, the NDT inspector 276 may initiate a collaboration session with the NDT inspector 278 via the cloud 24. For example, in one embodiment, the NDT inspector 278 may use the client-computing device 274 to broadcast a status such that each inspector connected to the NDT collaboration system 270 may be aware of the status. The status may indicate the availability, expertise, or other relevant information with regard to the NDT inspector 278. In certain embodiments, the NDT collaboration system 270 may store information related to the NDT inspector 278 such as a profile that indicates his experience, technical specialties, certifications, and the like.

When initiating the field request for support, the NDT inspector 276 may search through a list of experts or NDT inspectors 278, who may be indicated as being available via the NDT collaboration system 270. Once the NDT inspector 276 selects which NDT inspector 278 they may wish to seek assistance from, the NDT inspector 276 may send a request to the respective NDT inspector via a notification message that may be include information or an interface from which a collaboration session may be initiated. In certain embodiments, the notification message may be sent to the NDT inspector 278 via e-mail, text message, automated call, or the like. The notification message may include information suitable for initiating a collaboration session, such as a URL link, a whiteboarding session link, and the like, suitable for real time or near real time collaboration.

After the NDT inspector 276 initiates the collaboration session, the NDT collaboration system 270 may share the data depicted on the mobile device 22 with the remote NDT inspector 278 via the client-side computing device 274 in real time. During this real-time collaboration, the mobile device 22 may be controlled by the NDT inspector 276 via the mobile device 22 or by the NDT inspector 278 via the client-computing device 274. In one embodiment, the NDT inspector 276 may pass control of the screen depicted on the mobile device 22 to the NDT inspector 278 for remote control of the mobile device 22 or the NDT inspection device being controlled by the mobile device 22. When the NDT inspector 278 has remote control of an NDT inspection device, certain features on the NDT inspection device may be disabled for safety reasons. That is, the mobile device 22 may not allow the NDT inspector 278 to remotely control some features of the NDT inspection devices, which may place the NDT inspector 276 in an undesired situation. As such, in these cases, the mobile device 22 may disable the respective features of the NDT inspection device. For example, the mobile device 22 may disable the functionality of an x-ray inspection device or any other NDT inspection device that may initiate physical movements to enhance the safety of the NDT inspector 276.

In certain embodiments, the NDT inspector 276 may enable the mobile device 22 to be shared in real time by providing an input to the application being executed or running on the mobile device 22. As such, if the input is engaged by the NDT inspector 276, the application may send data related to the images and controls displayed on the mobile device 22 to the client-computing device 274 directly using a wired or wireless interface or indirectly via the cloud 24. Moreover, the NDT collaboration system 270 may also share the video streams, audio streams, chat streams, data streams, screen images, and the like available on the mobile device 22 and the client-side computing device 274 to add more context to the screen sharing. Data streams may include numerical data values or other external data such as temperature or humidity data that may be detected from the ambient air using sensors disposed on the mobile device 22, the NDT inspection device 12, or the like. In one embodiment, the data streams may be received by the mobile device 22, the NDT inspection device 12, or the like by interacting or via communicating with the asset being inspected. In any case, the additional sharing of video streams, audio streams, data streams, chat streams, screen images, and the like may help provide more context to the real-time data sharing session for both the NDT inspector 276 and the NDT inspector 278.

Additionally, the NDT collaboration system 270 may enable the NDT inspector to access and use NDT measurement and analysis tools running on the mobile device 22 to diagnose and/or analyze the NDT data. That is, during a collaboration session between the NDT inspector 276 and the NDT inspector 278, the NDT inspector 278 may use NDT measurement tools on the mobile device 272 to diagnose or analyze inspection results or NDT data received by the mobile device 22. For instance, the NDT inspector 278 may use various measurement tools, image processing tools, signal-processing tools, and the like to further analyze the NDT data.

In certain embodiments, the measurement and analysis tools may include collaboration tools such as virtual whiteboarding tools. The virtual whiteboarding tools may enable either the NDT inspector 276 or the NDT inspector 278 to superimpose writings or drawings onto images that depict the shared data. For instance, the virtual whiteboarding tools may enable the NDT inspector 276 or the NDT inspector 278 to write onto the shared data with a virtual pen to draw circles, arrows, or the like. Moreover, the virtual whiteboarding tools may also enable the the NDT inspector 276 or the NDT inspector 278 to add text annotations onto the shared data. As a result, the NDT inspector 276 and the NDT inspector 278 may better collaborate, troubleshoot, discuss, and analyze with each other using the virtual whiteboarding tools.

In one embodiment, the NDT collaboration system 270 may provide a connection to the database 272, which may include a knowledge base system that may include contextual information related to the NDT data, analysis of the NDT data, or the like. The knowledge base system may include a historical archive of inspection results and reports related to NDT devices, documents (drawings, videos, specifications etc.) related to NDT devices, documents related to the inspection procedure type (e.g., UT TOFT Weld, ET-Surface etc.) and any other related documents. As such, the knowledge base system may make all the relevant documents related to the inspection that is being carried out both for the NDT inspector 276 and the NDT inspector 278. In one embodiment, the knowledge base system may also provide other analytical information based on the historical inspection results. For example, the knowledge base system may indicate how a crack on a particular blade on the aircraft system 54 may have grown over time.

In certain embodiment, the database 272 may also store a recording of the whole session of collaboration between the NDT inspector 276 and the NDT inspector 278. The recording of such a session may be manually initiated by the NDT inspector 276 or the NDT inspector 278 or may be configured for automatic recording. The recording may be archived for future reference or may be used for training new NDT inspectors or for historical references such as previously completed audits.

Figure 12:
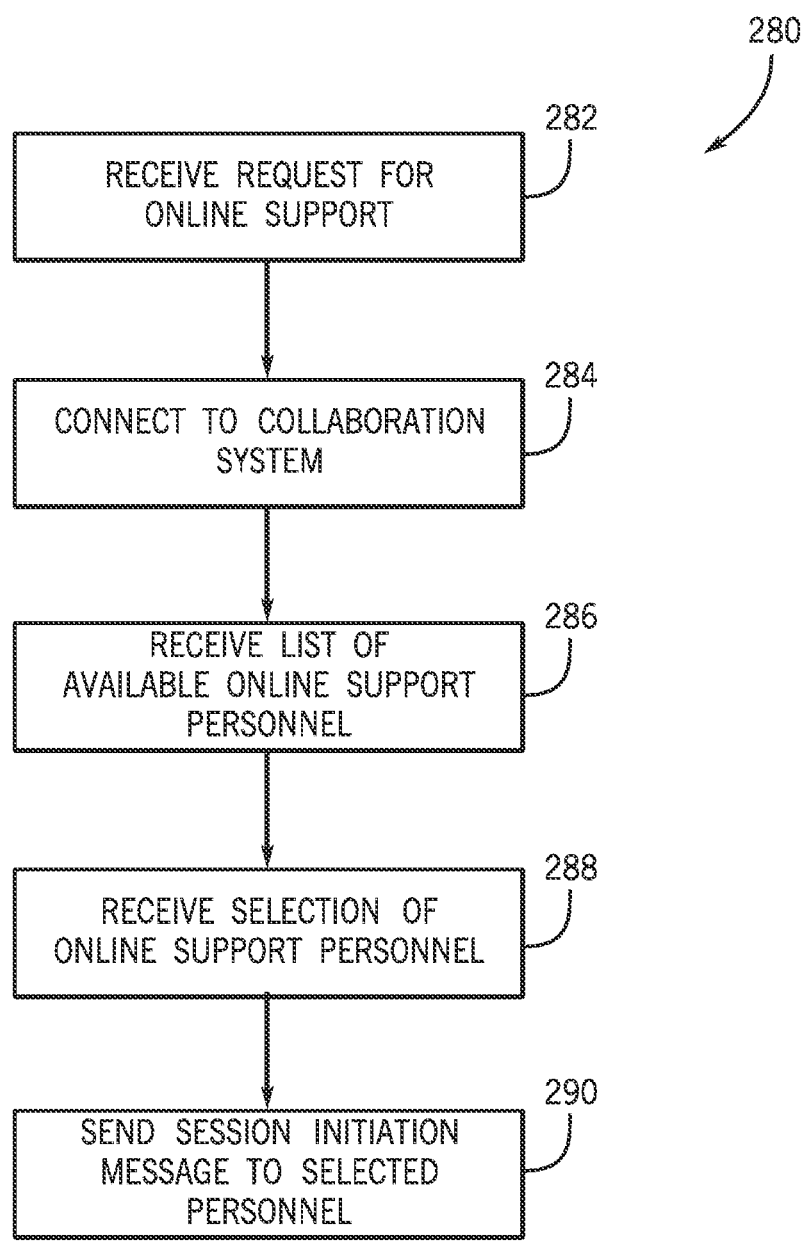
FIG. 12 is a flowchart of an embodiment of a process for sharing a display and control of a computing device using the collaboration system of FIG. 11, in accordance with aspects of the present disclosure.
Figure 13:
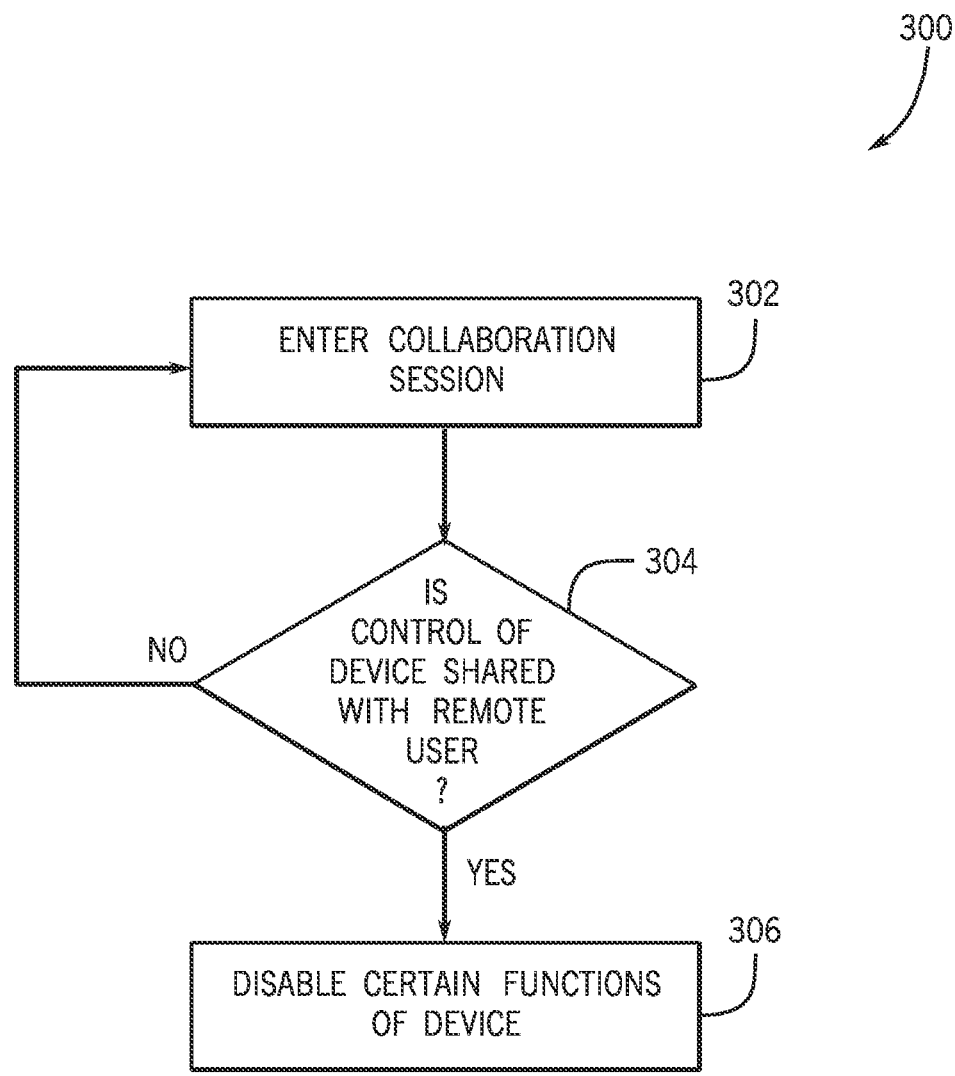
FIG. 13 illustrates a flowchart of an embodiment of a process for disabling certain functions of a device in the NDT system of FIG. 1 using the collaboration system of FIG. 11, in accordance with aspects of the present disclosure.

Keeping the foregoing in mind, FIG. 12 illustrates a method 280 for sharing display data and control of the mobile device 22, for example, via the NDT collaboration system 270. In one embodiment, an application in the mobile device 22 may be used to perform the process described herein. At block 282, the application may receive a request for online support. As mentioned above, the application may receive the request via an input interface displayed on the screen of the mobile device 22. In some embodiments, the request may include the type of equipment under inspection, the type of issues currently found (e.g., cracks, corrosion), the type of NDT inspection device(s) 12 in use, the level and expertise of the inspector(s) 276, the owner/lessee of the equipment undergoing inspection, and the like.

The application may, at block 284, connect to the collaboration system 270 via a wired or wireless communication, as described above. At block 286, the application may receive a list of individuals such as experts or entities that may be available to support the NDT inspector 276. In certain embodiments, the application may receive the list of individuals without connecting to the collaboration system 270. As such, the application may receive the list of individuals based on a list of contacts that may be stored locally in the device executing the application.

The list of individuals may include one or more individuals or groups of individuals that may have relevant expertise in one or more areas of NDT procedures, techniques, results, or the like associated with the application currently being executed by the mobile device 22. In certain embodiments, the list of individuals may be organized based on a level of expertise in the respective application, NDT inspection process, NDT device, or the like. As mentioned above, the NDT inspectors 278 may broadcast their status (e.g., availability) and expertise level over the collaboration network 270.

At block 288, the application may receive a selection of one or more individuals or entities from the list received at block 286. After the selection has been received, at block 290, the application may send a session initiation or notification message to the selected individuals. Accordingly, one or more experts or expert entities may participate to aid in inspection 154 and/or analysis 156. As such, the respective NDT inspector 278 may receive a notification message that may include information or an interface (e.g., link) from which a collaboration session may be initiated. In certain embodiments, the notification message may be sent to the NDT inspector 278 via e-mail, text message, automated call, or the like.

By providing the NDT collaboration system 270, the NDT inspector 276 may perform his inspection tasks or data analysis with the assistance of one or more of the NDT inspector 278 in real time. As such, the amount of time in which the NDT inspector 276 may take to perform his tasks may decrease through the real-time collaboration and support from the NDT inspector(s) 278, who may be an expert. It is to be noted that, in some examples, the NDT inspector 278 may include software or hardware systems such as expert systems, expert logic reasoning systems, and the like, that may "answer" questions based on artificial intelligence (AI) techniques and knowledge repositories. Moreover, the NDT collaboration system 270 may bridge the knowledge gap of the NDT inspector 276 and the NDT inspector 278 through real-time sharing of analysis tools and recommendations provided by the NDT inspector 278. Further, by providing access to information related with the data being analyzed or the like using the knowledge base system, the analysis performed by the NDT inspector 276 may be more accurate. Additionally, by storing recorded collaboration sessions, the collaboration system 270 may provide improved training to the new inspectors based on historical scenarios.

In order to improve the safety operations of the NDT devices, it may be beneficial to control the operations of the certain NDT devices while the mobile device 22 is operating during a collaboration session. That is, given the hazardous nature of certain NDT devices, such as an x-ray inspection device, care should be taken to avoid operating the NDT device remotely without regard to the presence and location of the field-operating NDT inspector 276. Accordingly, FIG.

13 illustrates a method 300 that may be used to safely operate certain NDT devices while operating in a collaboration session.

At block 302, the application on the mobile device 22, which may be located within a close proximity to the NDT device it may control, may enter a collaboration session with a remote user such as the NDT inspector 278 via the cloud 24 and the client-computing device 274. While operating in the collaboration session, the application may enable real-time sharing of the application being executed on the mobile device 22 between the NDT inspector 276 and the NDT inspector 278. As such, the application may share data depicted on the screen of the mobile device 22, control of the mobile device 22 or the respective NDT inspection device, and the like.

At block 304, the application may determine whether the control of the mobile device 22 or the respective NDT inspection device operated via the mobile device 22 may be shared with a remote user such as the NDT inspector 278. If the control is indeed shared with a remote user, the application may proceed to block 306.

At block 306, the application may automatically disable certain operational functions of the NDT inspection device or certain options for control of the NDT inspection device via the mobile device 22. In certain embodiments, control may be retrieved by the NDT inspector 276 at any time to disable certain operational functions of the NDT inspection device or certain options for control of the NDT inspection device to ensure that the NDT inspection device is being operated safely. Referring back to the x-ray inspection device example, at block 306, the application may disable the emission of x-rays from the x-ray inspection device to ensure that x-rays of unsuspecting individuals may not be performed remotely. Although certain operational functions of the NDT inspection device may be disabled, the NDT inspector 278 may still be able to use the measurement and analysis tools on the mobile device 22 to further analyze, troubleshoot, or assist the NDT inspector 276.

In certain embodiments, the application may proceed to block 306 after a determination has been made that the NDT inspection device being controlled by the application corresponds to a hazardous or potentially hazardous NDT inspection device. For example, if the NDT inspection device is a PTZ camera, the application may not proceed to block 306 to disable certain feature of the PTZ camera because the remote operation of the PTZ camera may not create a hazardous environment.

Referring back to block 304, if the application determines that the control is not shared with a remote user, the application may return to block 302 and remain in the collaboration session. As such, the NDT inspector 276 may continue to share the data depicted on the screen of the mobile device 22.

In addition to the features described above, the NDT collaboration system 220 may also enable data being depicted on the NDT device 12 or being generated on the mobile device 22 to be streamed onto the client-computing device 274. As such, the NDT collaboration system 270 may allow NDT inspector 276 to stream their NDT inspection live to the NDT inspector 278 while running an application, menu-driven interface, or the like. In certain embodiments, using location awareness technology, the NDT collaboration system 270 may also provide the NDT inspector 278 with applicable and relevant information stored on the database 272 related to a specific asset or component currently being displayed or inspected. For instance, relevant information may include data fields that correspond to an inspection report for an inspection process currently being performed. Additionally or alternatively, the relevant information may include historical NDT data related to the assets, NDT data for other like assets, measurement information associated with the respective NDT device 12 or the assets, measurement limits associated with the respective NDT device 12 or the assets, service bulletins associated with the respective NDT device 12 or the assets, technical manuals associated with the respective NDT device 12 or the assets, updated technical specifications associated with the respective NDT device 12 or the assets, original equipment manufacturer (OEM) recommendations associated with the respective NDT device 12 or the assets, industry standard operating procedures (SOP), maintenance shop manuals, and the like. As such, the mobile device 22 may stream live its current inspection data including information with regards to the asset it is inspecting and the respective location within that asset. Moreover, using this information, the NDT collaboration system 270 may automatically retrieve information to provide the NDT inspector 276 and the NDT inspector 278. Accordingly, the relevant information may be made available to both the NDT inspector 276 and the NDT inspector 278 to better enable either inspector to analyze the data and inspection process.

Figure 14:
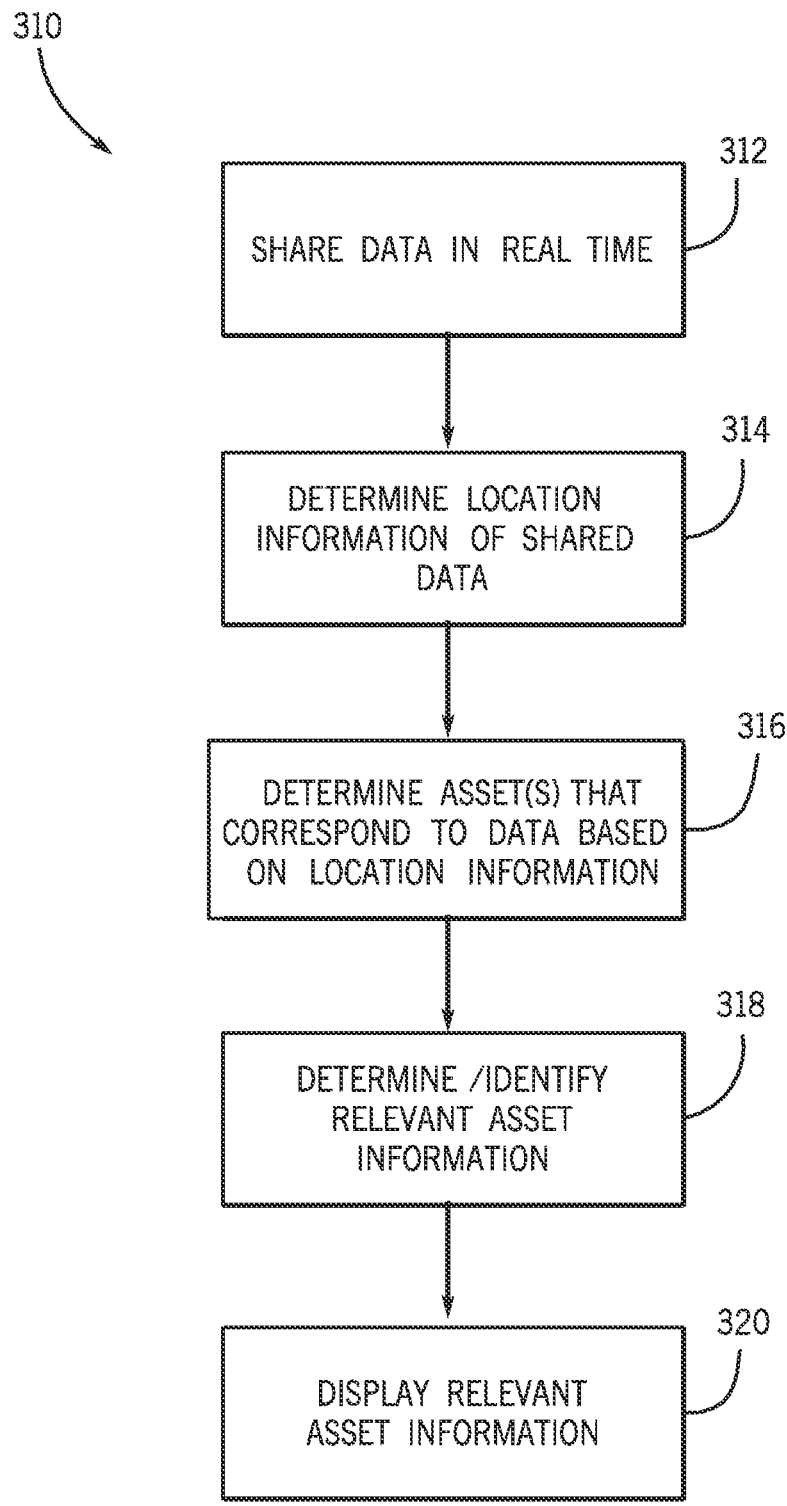
FIG. 14 illustrates a flowchart of an embodiment of a process for providing location aware data while inspecting a device in the NDT system of FIG. 1 using the collaboration system of FIG. 11, in accordance with aspects of the present disclosure.

Keeping the foregoing in mind, FIG. 14 illustrates a process 310 for providing location aware data while retrieving data from the NDT inspection devices 12. Like the processes described above, the process 310 or portions of the process 310 may be included in non-transitory computer-readable media stored in memory, such as the memory 15, 19, 23, 25, 93, 97, 101 and executable by one or more processors, such as the processors 17, 21, 25, 95, 99, 103, the computing system 29, and the cloud 24.

In one embodiment, an application containing computer instructions executable by the mobile device 22, the NDT inspection devices 12, computing system 29, and/or the cloud 24 may be used to collect data that may be related to the inspection of a piece of equipment (e.g., devices 12, 14, 16, 22, 42, 44, 46) within the NDT system 10 or may be used to generate reports 159 related to the NDT system 10. Although the process 310 depicts a particular order in which the process 310 may be performed, it should be noted that the process 310 may also be performed in a different order.

Referring now to FIG. 14, at block 312, the application may enter into a mode in which it shares data with one or more recipients in real time as described above. While sharing the data, at block 314, the application may determine location information associated with the shared data. Location information may include a physical location within equipment (e.g., turbomachinery 18) being inspected by the respective NDT inspection device 12. For instance, in the case of equipment such as the turbomachinery 18, the location information may indicate whether the data displayed on the mobile device 22 or the data retrieved by the mobile device 22 corresponds to a combustion chamber of the turbomachinery 18, a compressor of the turbomachinery 18, or the like.

In certain embodiments, the application may determine the location information based on the data being retrieved by the mobile device 22 from the NDT inspection device 12 and other information related to the inspection process such as the type of equipment being inspected, an amount of time in which the inspection has been in progress, empirical data related to the inspection process employed by the NDT inspector 276, and the like. For example, the application may determine that the data being entered into the mobile device 22 may be associated with the combustion chamber of the turbomachinery 18. As such, the application may determine that the mobile device 22 may located in the combustion chamber of the turbomachinery 18.

In another example, the application may determine an amount of time that has passed since the NDT inspector 276 started his inspection process and compare that time to the inspector's history or empirical data related to the inspector's previous inspections for similar equipment. Based on that comparison, the application may estimate or approximate which portion of the inspection process that the inspector may currently be and may determine a location within the respective equipment that may correspond to the portion of the inspection process that the inspector may currently be.

Further, determining a location [from empirical data?] may include monitoring NDT inspector's 276 position in a workflow, a Menu Driven Inspection (MDI) process, or an application or feature of NDT inspection device 12 or mobile device 22 that guides NDT inspector 276, i.e., a guided inspection application. Additionally, NDT inspector 276 or NDT inspector 278 may identify, tag, or otherwise enter the location information.

The mobile device 22 may also include additional circuitry or applications that may be used to determine the location information. For instance, the mobile device 22 may use indoor global positioning system (GPS) technology, image recognition technology, radio frequency identification (RFID) technology, barcode technology, optical character recognition (OCR) technology, triangulation (e.g., WiFi triangulation, radio triangulation) and the like to determine the location within the equipment being inspected. By way of example, if the shared data of block 312 includes a live video feed of an inspection being performed within an asset, the application may use image recognition software to identify certain parts of the equipment and determine a location within the equipment based on the identified parts. In the same manner, the application may receive inputs from the indoor GPS technology, RFID technology, barcode technology, OCR technology, and the like and compare the input data to a legend or key to determine the location within the equipment being inspected. The legend or key may be stored, in certain embodiments, in the database 222 or the like.

Keeping this in mind, at block 316, the application may determine or identify an asset or assets being inspected or that corresponds to the data being shared at block 262. The asset may correspond to a component within the equipment being inspected. For example, the assets of the turbomachinery 18 may include a combustion chamber, a compressor, or the like. In one embodiment, the application may determine or identify the asset based on the location information determined at block 314. Additionally or alternatively, the application may use the image recognition technology, the indoor GPS technology, RFID technology, barcode technology, OCR technology, triangulation, and the like to identify the asset being inspected. That is, the application may receive information from the image recognition technology, the indoor GPS technology, RFID technology, barcode technology, OCR technology, triangulation, and the like that may indicate the asset or type of asset related to the data received at block 312.

After identifying the assets that correspond to the data shared at block 312, at block 318, the application may determine or identify information related to the respective asset. That is, the application may identify relevant asset information based on the location within the asset that corresponds to the data shared at block 312. The relevant asset information may include inspection reports or any data entry tool that may be part of the inspection process or reporting that the NDT inspector 276 may perform. As such, as the NDT inspector 276 approaches a particular asset, the application may display a data field in an inspection report related to the particular asset. In this way, the NDT inspector 276 may more efficiently enter data by, for example, reduced interaction with the application.

In certain embodiments, the NDT inspector 276 and the NDT inspector 278 may also retrieve additional information related to the identified asset. As such, the relevant asset information may also include previous inspection data for the identified asset, inspection data for other like assets, measurement information for the identified asset, measurement limits for the identified asset, service bulletins or updates for the identified asset, technical manuals or updated technical manuals for the identified asset, original equipment manufacturer (OEM) recommendations for the identified asset, and the like.

The relevant information may be stored locally on the mobile device 22, the client-side computing device 274, or the like. Alternatively or additionally, the relevant information may be stored in the knowledge base system in the database 272. As such, the application may retrieve the relevant information from the database 272 via the cloud 24. In one embodiment, the application may display a tag or a brief text description of the relevant information related to the shared data on the screen of the mobile device 22. Here, the NDT inspector 276 or the NDT inspector 278 may retrieve the relevant information upon interacting with the tag or text description.

At block 320, the application may display the relevant information, or a prompt therefor, on the screen of the mobile device 22 or on the data being shared at block 312. For example, if the data being shared includes a video feed, the application may super impose a link or graphical user interface (GUI) icon or graphic, which may connect to the relevant information, or the information may be displayed in another window or screen of the GUI.

In other embodiments, the NDT collaboration system 270 may be used to perform various types of data analysis techniques. That is, the cloud 24 may include a computing network with a number of processors that may analyze data using various types of algorithms and the like. As such, the cloud 24 may be used to perform various types of analysis that may be computationally intensive or may not be performed efficiently on the mobile device 22 or the client-side computing device 274. The data analysis may be performed on the data acquired by the NDT inspection devices 12 and may include applying various types of algorithms (e.g., filters) to the data, generating visualizations that depict the data, and the like. In certain embodiments, the data analysis may include applying predictive analytic algorithms to the data to determine the useful life of an asset associated with the data or the like.

By employing servers and/or services in the cloud 24 to analyze data, the NDT inspector 276 and/or the NDT inspector 278 may analyze data captured by NDT inspection devices 12 using the processing capabilities of the cloud 24, as opposed to the processing capabilities of a local machine such as the mobile device 22 or the client-side computing device 274. In this manner, the NDT inspector 276 may acquire data via the mobile device 22 and the NDT inspection device 12 while performing an inspection operation in the NDT system 10. After acquiring the data, the mobile device 22 may automatically send the data to the cloud 24, which may be executing one or more customized algorithms on the data. After executing the algorithms, the cloud 24 may return the results or the analyzed data back to the mobile device 22 using the collaboration system 220.

As the cloud 24 receives the data, the cloud 24 may identify and save metadata regarding the data in a storage or memory within the cloud 24, the database 272, or the like. The metadata may include information that corresponds to the asset being inspected, the methods used to inspect that asset, measurements received from that asset, component identification information pertaining to that asset, and the like. In certain embodiments, the cloud 24 may categorize the metadata and store the metadata with respect to its categories. In other embodiments, the cloud 24 may analyze the data and/or metadata with respect to certain variables. For example, the cloud 24 may compare the data acquired by the NDT inspection device 12 to data previously acquired by the respective NDT inspection device 12, data acquired by a fleet of the NDT inspection devices 12, data acquired by like assets, known values (e.g., measurement gates), and the like.

Figure 15:
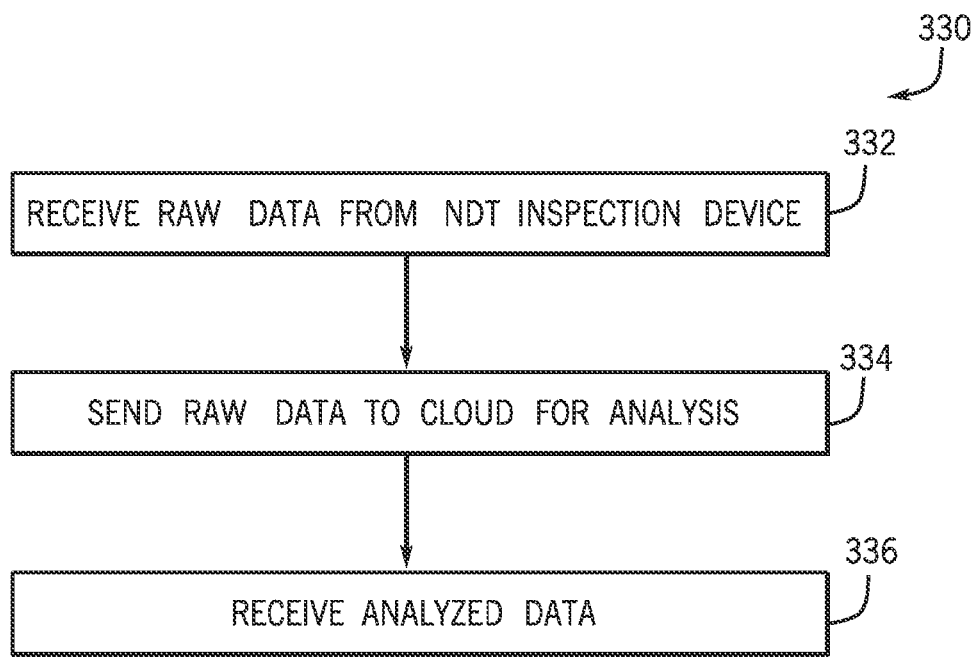
FIG. 15 illustrates a flowchart of an embodiment of a process for sending raw data that corresponds to the NDT system of FIG. 1 to a cloud-computing device in the collaboration system of FIG. 11, in accordance with aspects of the present disclosure.

Keeping the foregoing in mind, FIG. 15 depicts a flowchart of a process 330 that may be employed by the mobile device 22, the client-side computing device 274, the NDT inspection device 12, or the like to analyze NDT data using the collaboration system 270. In particular, the process 330 is related to analyzing data acquired by the NDT inspection device 12 using the cloud 24 of the NDT collaboration system 270.

In one embodiment, an application containing computer instructions executable by the mobile device 22, the client-side computing device 274, the NDT inspection devices 12, computing system 29, and/or the cloud 24 may be used to perform the process 330. Although the process 330 depicts a particular order in which the process 330 may be performed, it should be noted that the process 330 may also be performed in a different order.

Referring now to FIG. 15, at block 332, the application may receive raw data that may have been acquired by the NDT inspection device 12. The raw data may be identified or designated by the NDT inspector 276 or the NDT inspector 278 as data that should be analyzed using one or more algorithms. As such, in one embodiment, the application may send the raw data to the cloud 24 for analysis. That is, the cloud 24 may employ its processors to analyze the data, as opposed to the data being analyzed on the mobile device 22 or the client-side computing device 274, which may not have the same processing power as the cloud 24. For example, the cloud 24 may include one or more virtual machines (VMs), servers, storage, load balancers, network caching, and the like suitable for executing cloud computing analytics.

In certain embodiments, as the raw data is received by the NDT inspection device 12, the NDT inspector 276 or the NDT inspector 278 may indicate to the application one or more algorithms in which to process the raw data using the cloud 24. By analyzing the raw data using the processor(s) in the cloud, the NDT inspector 276 or the NDT inspector 278 may analyze the raw data more efficiently. That is, since the computing network of the cloud 24 may include scalable computing systems or processors and may, as a result, generally include more processing power than the mobile device 22 or the client-side computing device 274. In this way, the NDT inspector 276 or the NDT inspector 278 may continue the inspection process or analyze other data while the cloud 24 processes or analyzes data that may use more processing power than available on the mobile device 22 or the client-side computing device 274.

Figure 16:
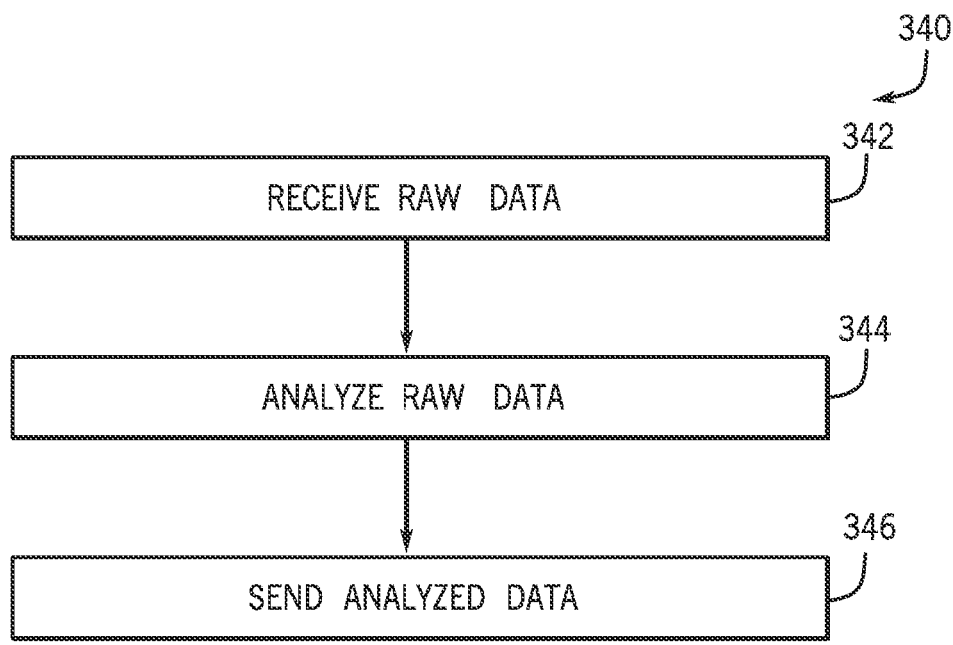
FIG. 16 illustrates a flowchart of an embodiment of a process for analyzing raw data that corresponds to the NDT system of FIG. 1 using a cloud-computing device in the collaboration system of FIG. 11, in accordance with aspects of the present disclosure.

Keeping the process 330 in mind, FIG. 16 illustrates a process 340 that the cloud 24 may employ when analyzing the raw data acquired by the mobile device 22 via the NDT inspection device 12. Like the mobile device 22, the cloud 24 may include an application (e.g., cloud application) that may include computer instructions executable by the cloud 24 to analyze the data acquired by the NDT inspection device 12. As such, at block 342, the cloud application may receive the raw data sent by the mobile device 22 (block 334). In addition to the raw data, the cloud application may receive an indication of one or more algorithms in which to analyze the received data. In certain embodiments, the algorithms may be customized algorithms that may be uploaded to the cloud 24 and designed by a developer of the application for the mobile device 22, a developer of the cloud application, a third-party developer, or the like.

At block 344, the cloud application may analyze the data received at block 342 using its respective processor(s). As such, the cloud application may analyze the data using the algorithms specified by the NDT inspector 276 or the NDT inspector 276 as described above. In one embodiment, the data analysis may be performed by the NDT inspector 276 or an expert connected to the cloud 24 using the data analysis tools available to the cloud 24. The data analysis tools may analyze the data for measurements associated with the asset being inspected, assisted and/or automatic defect recognition for the asset being inspected, disposition information on an asset and/or component being inspected, asset and/or component history, and the like. In one embodiment, the analyzed data may include one or more instructions for the NDT inspector 276 to acquire additional data, to revise the manner in which the data is acquired, or the like based on the results of the analysis.

By way of example, if the data received at block 342 is associated with ultrasound waveforms or data acquired while inspecting a weld, the ultrasound data may be received by the cloud 24 at block 342 and analyzed by an expert at block 344. As such, the expert may apply various filters on images that correspond to the ultrasound data, which may accentuate defects in the weld or remove various artifacts or noise from the ultrasound data, thus improving inspection analysis. In one embodiment, the cloud application may analyze the metadata received with the ultrasound data associated with the weld to determine possible types of defects (e.g., lack of penetration or fusion, existence of crack, etc.) that may present in the weld. The analysis performed by the cloud application may also include generating a report that may summarize the findings of the analysis, provide a summary of the data and the metadata acquired by the NDT inspection devices 12, provide a list of outcomes or recommendations associated with the findings, the data, or the metadata, and the like. For example, the report may list each defect that may be present with the weld. In each entry, the report may indicate additional information regarding the respective defect such as a size, location, and type of defect.

In another example, if the data received at block 342 is associated with eddy current inspection data, the cloud 24 may be used to analyze the eddy current inspection data at block 344. Eddy current data analysis may be performed by various sophisticated analysis algorithms useful in deriving observations of eddy currents traveling through ferrous or non-ferrous material, which may be executed more efficiently using the processing power of the cloud 24. In certain embodiments, various analysis algorithms may be performed multiple times for multiple iterations to obtain more accurate results. Again, by performing these types of calculations on the cloud 24, as opposed to the mobile device 22 or the client-side computing device 274, the NDT inspector 276 and/or the NDT inspector 278 may obtain more accurate analysis data more efficiently.

In yet another example, the cloud 24 may also be used to analyze radiography data. Here, the NDT inspector 274 or an expert may analyze the radiography data using the cloud 24. For instance, the cloud 24 may be used to apply a Flash Filter™ or other similar analysis tools to the radiography data.

In certain embodiments, the data received at block 342 may be received continuously such that the data is streaming into the cloud 24. As such, at block 344, the cloud 24 may continuously analyze the data as it is streamed into or received by the cloud 24.

After the raw data has been analyzed, at block 346, the cloud application may send the analyzed data back to the respective mobile device 22 or the respective client-side computing device 274 that sent the data received at block 342. As such, the NDT inspector 276 or the NDT inspector 278 may receive the results of the analysis and continue the inspection or data gathering process based on the results.

Figure 17:
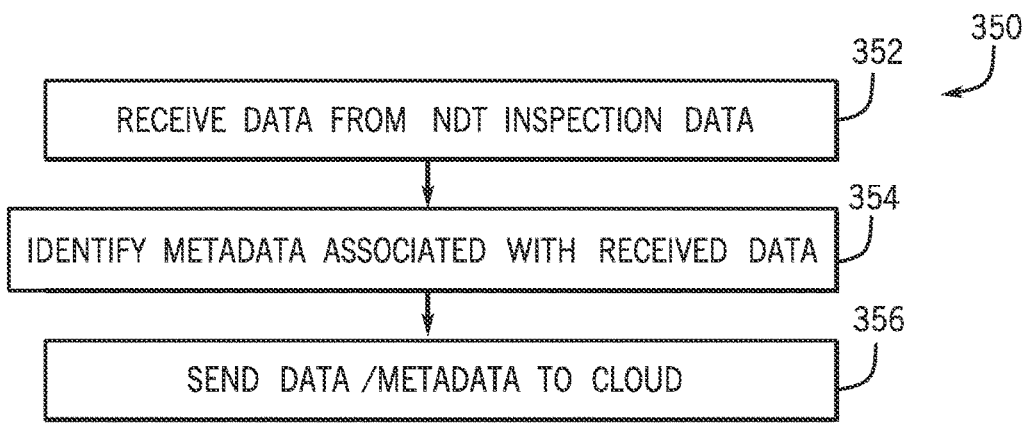
FIG. 17 illustrates a flowchart of an embodiment of a process for sending data that corresponds to the NDT system of FIG. 1 to a cloud-computing device in the collaboration system of FIG. 11, in accordance with aspects of the present disclosure.

In addition to analyzing the data using the cloud 24, the NDT collaboration system 270 may be used to organize and/or categorize data acquired by the NDT inspection devices 12. FIG. 17 depicts a process 350 for sending data and/or metadata acquired by the NDT inspection device 12 via the mobile device 22 to the cloud 24.

Like the process 330 of FIG. 17, an application containing computer instructions executable by the mobile device 22, the client-side computing device 274, the NDT inspection devices 12, computing system 29, and/or the cloud 24 may be used to perform the process 350. Moreover, although the process 350 depicts a particular order in which the process 350 may be performed, it should be noted that the process 350 may also be performed in a different order.

Referring now to FIG. 17, at block 352, the application may receive data acquired by the NDT inspection device 12. The application may then, at block 354, identify metadata associated with the data received at block 352. The metadata may include information that corresponds to the asset being inspected, the methods and/or inspection protocols being used to inspect the asset, measurements associated with the assets, component identifications that may be part of the asset, and the like. After identifying the metadata, at block 356, the application may send the data and/or the identified metadata to the cloud 24, which may analyze and/or organize the data and/or the metadata as described below with reference to FIG. 18.

Figure 18:
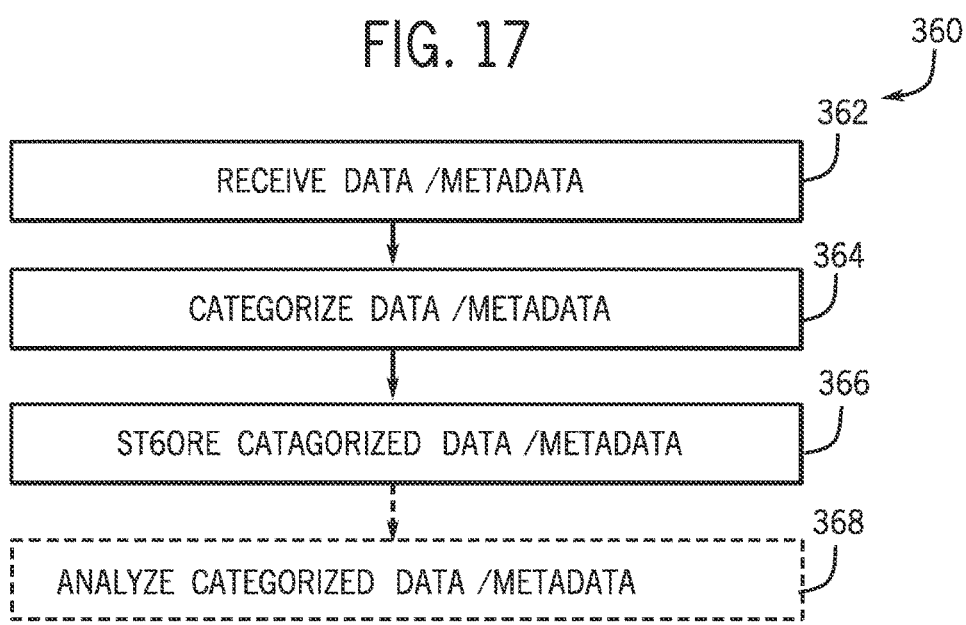
FIG. 18 illustrates a flowchart of an embodiment of a process for organizing and analyzing data that corresponds to the NDT system of FIG. 1 using a cloud-computing device in the collaboration system of FIG. 11, in accordance with aspects of the present disclosure.

Keeping this in mind, FIG. 18 depicts a flowchart of a process 360 that may be used by the cloud application to organize data and/or metadata received from the mobile device 22 or the like. As such, at block 362, the cloud application may receive data and/or metadata from the mobile device 22 or any other device coupled to the cloud 24. The data received at block 362 may have been acquired by the NDT inspection device 12 as described above. In the same manner, the metadata may have been identified by the application executing in the mobile device 22 as described above with reference to FIG. 17. In one embodiment, the cloud application may identify or extract the metadata from the received data.

In any case, at block 364, the cloud application may categorize or organize the data and/or metadata. For instance, the cloud application may categorize the data and/or metadata based on the asset being inspected, whether the asset being inspected is part of a fleet of assets, the inspection process used to inspect the respective asset, and the like.

The fleet of assets may include a group of assets of a particular type, model, or group that may be in service at various locations. When data is categorized according to its fleet, the cloud application may be capable of performing additional data analysis using the data acquired from similar assets of the same fleet. For example, a first entity may use a particular asset for a chemical processing plant while a second entity may use the same type of asset for a packaging plant. Each asset operating in different environments may operate under different conditions. As such, the first entity may be interested in knowing how the asset may operate under conditions that may be similar to how the packaging plant uses the asset, while the second entity may be interested in knowing how the asset may operate under conditions that may be similar to how the packaging plant uses the asset. By categorizing the data and the metadata associated with the same type of asset together, the cloud application may build an inventory of data that may be analyzed to determine more details as to the operations, operational life, capabilities, and the like with regard to the particular asset.

In one embodiment, the cloud application may alter or modify the data and/or metadata such that the owner of each asset may be anonymous. For instance, the cloud application may remove any information in the data and/or metadata that may indicate where the asset is installed, who the asset has been purchased by, and the like. In this manner, the asset owners may be inclined to allow the cloud application to categorize their respective data as part of its respective fleet without providing sensitive details as to their particular processes or operations.

At block 366, the cloud application may store the categorized data and/or metadata in a memory. In one embodiment, the categorized data and/or metadata may be stored in the database 272 or the like. As such, the categorized data and/or metadata may be available to the NDT inspector 276, the NDT inspector 278, an expert, or the like for analysis. That is, the NDT inspector 276, the NDT inspector 278, the expert, or the like may analyze data that corresponds to its respective asset with respect to data in various categories.

In certain embodiments, at block 368, the cloud application may analyze the categorized data and/or metadata to determine trends, operational life, maximum and minimum parameters, and various other types of details with regard to each category of data. The cloud application may also generate a report that may summarize the analysis performed by the cloud application. After analyzing the categorized data and/or metadata, the cloud application may send the results of the analysis (e.g., report) back to the mobile device 22 or the like. It should be noted that when the mobile device 22, the client-side computing device 274, the cloud 24, or the like sends data or information within the collaboration system 270, the data may be encrypted prior to being sent and decrypted once received to protect the integrity of the data or information being sent.

In addition to the above-described processes for analyzing data acquired by the NDT inspection devices 12, the mobile device 22 or the cloud 24 may provide a way in which various review and analysis protocols or workflows may be implemented for data acquired from different NDT inspection devices 12. That is, an application executed by the mobile device 22, the cloud 24, the client-side computing device 224, or the like may be used to define a workflow for reviewing or analyzing data (NDT data) acquired by the NDT inspection devices 12 based on the type of NDT data that is being analyzed. In other words, the NDT inspector 276 may use a single platform to review and analyze various types of NDT data, regardless of which type of NDT inspection device 12 was used to collect the NDT data. That is, the techniques described herein may provide a flexible, multimodal approach in performing a comprehensive analysis on an asset being inspected, as opposed to being limited to a specific mode of analysis (e.g., x-ray).

In conventional NDT data analysis systems, however, the available review and analysis applications provide only one analysis protocol or workflow for all types of NDT data (e.g., ultrasound, eddy current, radiography, visual inspection etc.). As such, the workflows, data presentation layouts, and data analysis tools provided by the conventional NDT data analysis systems are fixed and rigid. As a result, users of the conventional NDT analysis systems may be limited in performing various review and analysis techniques. Moreover, less experienced users may find it difficult to properly review and/or analyze the NDT data using the workflow provided by the conventional NDT data analysis system since the conventional NDT data analysis system may provide too many options for analysis (e.g., providing x-ray analysis tools when receiving eddy current NDT data).

Keeping this in mind, the techniques described herein may enable an application executed by the mobile device 22, the cloud 24, the client-side computing device 224, or the like to provide a particular workflow for reviewing and analyzing NDT data based on the type of NDT data being reviewed. The workflow may include displaying the NDT data according to a pre-configured layout, providing a particular set of tools to analyze the respective NDT data, pre-processing the NDT data according to viewer presets or other image pre-processing rules, and the like. The workflow may also include generating reports based on the analyzed NDT data, automatically sending inspection results, reports, or the like. Additionally, the workflow may include retrieving various types of reference material such as reference codes, drawings, and user-interface elements that may simulate the actual inspection process to provide additional context to the user when reviewing or analyzing the NDT data.

In certain embodiments, the workflow may be encoded within the application and may be retrieved by the application based on a template being used to analyze the NDT data. The template may be prepared with a common set of semantics such that the same template may be used in any computing device such as a desktop-based review station or a web/cloud-based review station (e.g., mobile device 22, cloud 24, or client-based computing device 278). Such a template may be associated with metadata associated with certain inspection results. For example, the application may retrieve a template to review or analyze the NDT data based on the metadata associated with the NDT data. In this case, once the application retrieves the appropriate template, the template may dictate to the application a workflow in which to review and analyze the NDT data. As such, the workflow may indicate to the application to present a particular review and analysis screen with a particular screen, layout, set of tools, set of presets etc. In one embodiment, the workflow may execute a particular data analysis application that may be used to analyze the particular NDT data acquired by the NDT inspection devices 12.

In other embodiments, the platform or operating system used to perform the NDT data analysis may determine or identify an appropriate workflow for the NDT data currently being displayed or accessed by the NDT inspector 276, the NDT inspector 278, an expert, or the like. In this case, the platform may dynamically change the application being used to analyze the NDT data, dynamically change the data analysis tools provided, or the like based on the NDT data currently being accessed. For example, if the platform is currently providing data analysis tools that may be used to analyze eddy current data, the platform may dynamically change the data analysis tools being provided to data analysis tools for analyzing x-ray data when the platform receives x-ray data for review or analysis. That is, the platform may recognize that x-ray information is currently being viewed or accessed, and as a result, the platform may provide x-ray data analysis tools for the user.

Figure 19:
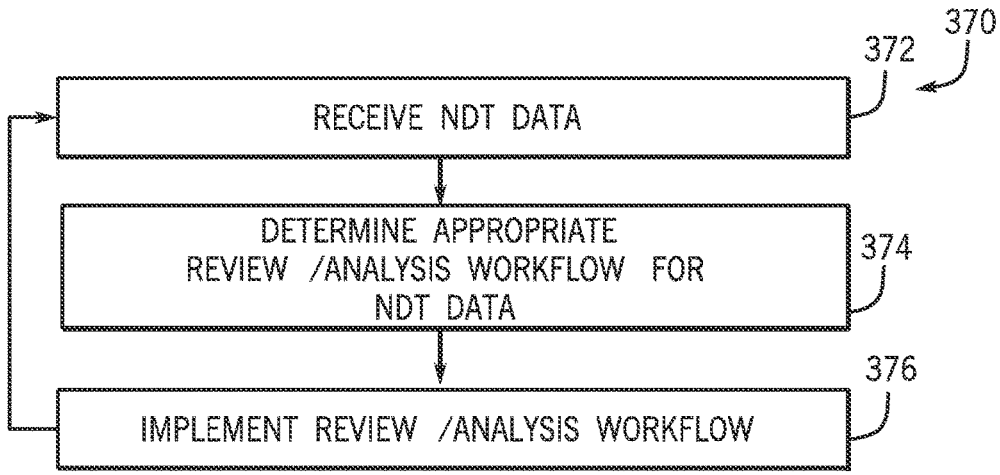
FIG. 19 illustrates a flowchart of an embodiment of a process for implementing a workflow for reviewing and/or analyzing data that corresponds to the NDT system of FIG. 1, in accordance with aspects of the present disclosure.

Keeping the foregoing in mind, FIG. 19 depicts an embodiment of a process 370 for implementing a workflow for reviewing and/or analyzing NDT data acquired by the NDT inspection devices 12. In one embodiment, an application containing computer instructions executable by the mobile device 22, the client-side computing device 274, the NDT inspection devices 12, computing system 29, and/or the cloud 24 may be used to perform the process 370. Although the process 370 depicts a particular order in which the process 370 may be performed, it should be noted that the process 370 may also be performed in a different order.

At block 372, the application may receive data (NDT data) acquired by the NDT inspection devices 12. In certain embodiments, the NDT data may be received by the cloud 24 such that the analysis of the NDT data may be performed on the cloud 24. As such, the NDT data analysis workflows and/or tools may not be limited by the capabilities of a local device such as the mobile device 22 or the client-side computing device 278.

In any case, at block 374, the application may determine an appropriate user workflow to implement for reviewing and analyzing the received NDT data. The user workflow may specify a set of processes, methods, or the like in which the application may implement when the NDT data is being reviewed or analyzed. Moreover, the user workflow may also define one or more individuals (e.g., experts) or entities that may have access to the NDT data or may be requested to review and/or analyze the NDT data. Additionally, the workflow may define who may receive a report or analyzed NDT data after a report has been generated or the NDT data has been analyzed.

In general, the user workflow may define a process in which the user of the application may employ when reviewing and analyzing the NDT data. That is, the workflow may define a particular set of NDT data processing steps to use when analyzing or reviewing the NDT data. For instance, when reviewing radiography data, the corresponding workflow may automatically apply certain filters to the images that correspond to the radiography data to remove noise and other undesired artifacts that may be present in the images. In certain embodiments, the application may use the user workflow to ensure that the review/analyzer (e.g., NDT inspector 278) follows the entire user workflow. For instance, the application may prohibit the reviewer from performing various types of analysis or the like until certain techniques or processes have been implemented.

The user workflow may also include applying various pre-processing algorithms to the NDT data such as applying filters and the like to remove noise from image data. Additionally, the user workflow may define post-processing steps such as sending the NDT data to other data processing centers, creating reports based on the NDT data or the analyzed NDT data, sending the reports to various personnel in the NDT system 10, and the like. Each of these user workflow processes may be implemented automatically by the application to help enable the user to review and/or analyze the NDT data more effectively and efficiently. Moreover, the application may help ensure that the user employs the appropriate user workflow process when reviewing and/or analyzing the NDT data. In this manner, the application may ensure that the NDT data is reviewed and/or analyzed according to a specified procedure.

Referring back to block 374, the appropriate user workflow for the NDT data may be determined based on a mode in which the application may be executed, a type of NDT inspection device 12 used to acquire the NDT data, the NDT methodology employed to acquire the NDT data, and the like. The appropriate workflow may also be defined in metadata associated with the NDT data. That is, the metadata may indicate the type of NDT data that may be received, the appropriate user workflow to implement for analyzing the NDT data, or the like. Using the information provided by the metadata, the application may then determine an appropriate user workflow for reviewing and/or analyzing the NDT data.

In certain embodiments, the user workflow may be customized based on the NDT data being reviewed or analyzed. That is, different types of NDT data may use different user workflows when analyzing the respective NDT data. For instance, eddy current data may differ significantly from radiography data. As such, the review and/or analysis processing steps and/or tools used to analyze the respective NDT data may differ significantly. In this way, the user workflow determined at block 374 may correspond to the type of NDT data being analyzed such that the process for reviewing and/or analyzing the NDT data may be performed more efficiently.

After determining the appropriate user workflow, at block 376, the application may implement the appropriate workflow as described above. As such, the application may verify that the user perform various steps in the user workflow with the NDT data before proceeding to other steps. The application may also display messages or instructions that specify how the NDT data may be analyzed according to the workflow. In certain embodiments, after implementing the user workflow at block 376, the application may repeat the process 370 such that the user workflow may change dynamically based on the NDT data being reviewed (i.e., received at block 372).

By automatically implementing the workflow for the NDT data analysis review, the application may make the make reviewing and analyzing the NDT data more efficient. That is, the workflow-based application may help improve the inspection workflow process and thus save time for the user reviewing or analyzing the NDT data. Moreover, the application may also ensure that a particular process or certain review rules are performed by the reviewer by encoding the workflow to prevent the reviewer from proceeding to certain steps in the workflow until other steps have been completed.

Figure 20:
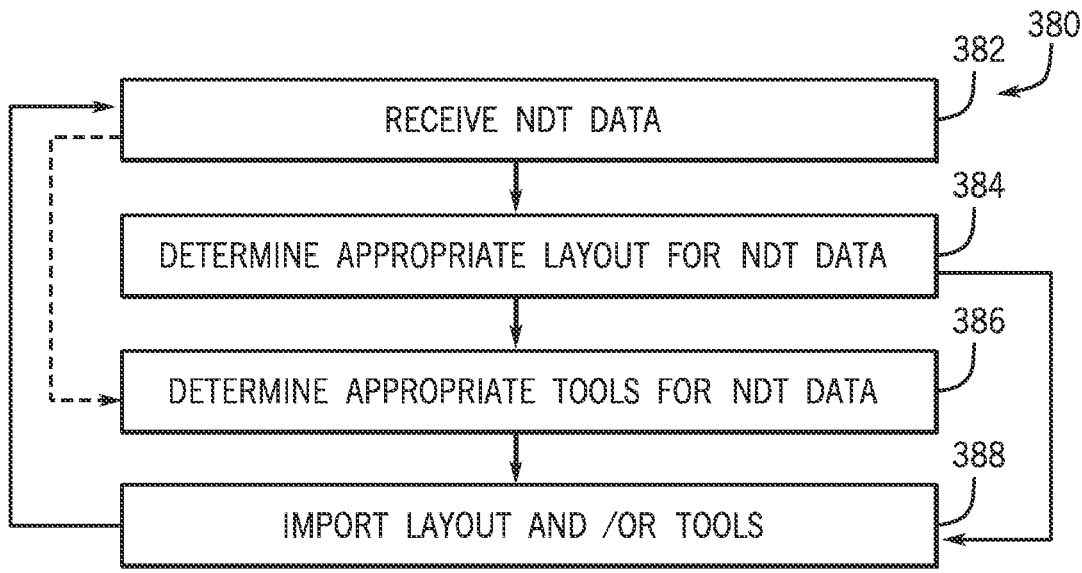
FIG. 20 illustrates a flowchart of an embodiment of a process for preparing data that corresponds to the NDT system of FIG. 1 for analysis via the collaboration system of FIG. 11, in accordance with aspects of the present disclosure.

The application may also generate an appropriate layout to display the NDT data and data analysis tools that may be used to analyze the NDT data. FIG. 20 illustrates a flowchart of a process 380 that may be used to display the appropriate layout and tools for a user. At block 382, the application may receive NDT data as described above with respect to block 372. That is, the NDT data may be received by the application such that it may be reviewed or analyzed.

After receiving the NDT data, at block 384, the application may determine an appropriate layout in which to display the NDT data. In certain embodiments, the application may determine the appropriate layout based on a modality (e.g., eddy current, radiography, etc.) that corresponds to the application being executed. In another embodiment, the application may determine the layout based on an indication received from the user via an input device such as a keyboard, keypad, or the like. In yet another embodiment, the application may determine the layout based on the asset or component in which the NDT data represents. As such, the application may present the NDT data using a particular layout or in a particular graphical mode based on the mode in which the application is operating, an input received from the user of the application, the type of NDT data being analyzed, accessed, or displayed, or the like. In certain embodiments, this information may be embedded within metadata associated with the received NDT data.

The layout may, in some cases, be pre-determined by the user of the application according to his preferences for reviewing and/or analyzing the NDT data. Alternatively, the application may determine the particular layout based on the NDT data and historical references with regard to layouts used to analyze the respective NDT data. The layout may include a manner in which the NDT may be organized or presented to the user. For example, the NDT data may be organized according to specific assets being inspected, times and/or dates in which inspections occurred, particular jobs associated with an inspection, or the like.

After receiving the NDT data at block 382 or determining the appropriate layout for the NDT data at block 384, at block 386, the application may determine an appropriate data analysis tools that may be used to analyze the NDT data received at block 382. In one embodiment, the set of data analysis tools may be defined in the user workflow described above with reference to FIG. 19. Otherwise, the application may independently determine the set of data analysis tools based on the NDT data being accessed, the metadata associated with the NDT data, an indication received from the user of the application, or the like. In any case, the set of data analysis tools may cater to the type of NDT being analyzed. That is, each type of NDT data (e.g., eddy current, radiography, ultrasound, visual) may be associated with a specific set of tools that may be used to analyze and/or review the NDT data. For instance, the set of data analysis tools may include various image filters when the NDT data corresponds to radiography data; however, the set of data analysis tools may not include the image filters when the NDT data corresponds to eddy current data since eddy current data may not include any images.

After determining the appropriate layout to display the NDT data and/or the appropriate set of data analysis tools for the NDT data, at block 388, the application may import the layout and/or the set of data analysis tools for the user to review and/or analyze the NDT data. In one embodiment, the set of data analysis tools may be displayed on the screen of the mobile device 22, the client-side computing device 272, or the like according to the layout. After importing the layout and/or data analysis tools, the application may repeat the process 380 for each time NDT data is received by the application. As such, the application may dynamically change the layout and/or data analysis tools based on the NDT data currently being accessed or analyzed.

In certain embodiments, a different set of data analysis tools may be imported for different parts of the user workflow. That is, different parts of the user workflow may include different types of data analysis techniques that may use different types of data analysis tools. By continuously importing the appropriate data analysis tools while the user analyzes or reviews the NDT data according to the user workflow, the application may enable the user to efficiently analyze the NDT data. Moreover, by providing the appropriate data analysis tools as the user analyzes the NDT data according to the user workflow, the application may assist less-experienced users (i.e., reviewers) by automatically selecting the data analysis tools that may be of use to them. Further, automatically providing the data analysis tools may also help experienced users by simplifying the data analysis tools provided in the user interface of the application or by providing the appropriate data analysis tools without any input from the user.

Although the process 370 and the process 380 described above may be performed by the NDT inspector 276, the NDT inspector 278, or the like using the mobile device 22, the client-side computing device 274, or the like, it should be noted that the process 370 and the process 380 may be used in conjunction with the cloud 24 to enable an individual (e.g., an expert) to log into the application via the cloud independent of any inspection procedure. That is, the expert may access NDT data via the cloud 24 using the application, and the application may, in turn, enable the expert to view and analyze all types (e.g., modalities) of NDT data using a number of user workflows, layouts, data analysis tools, and the like. As such, the expert is given an opportunity to receive a comprehensive view into the health or status of an asset or component that has been inspected.

Figure 21:
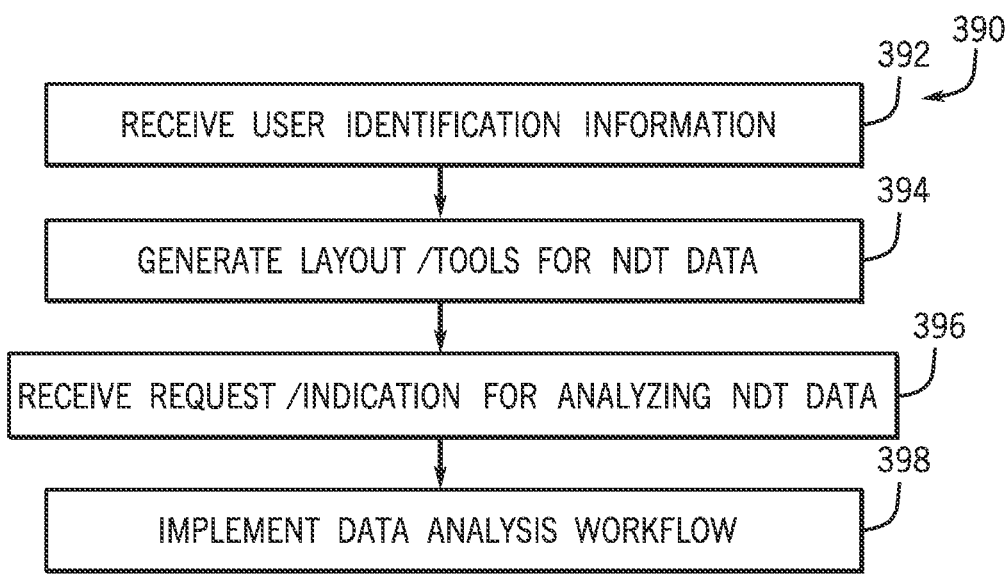
FIG. 21 illustrates a flowchart of an embodiment of a process for analyzing data that corresponds to the NDT system of FIG. 1 for analysis via the collaboration system of FIG. 11, in accordance with aspects of the present disclosure.

Keeping this in mind, FIG. 21 depicts a process 390 that may be used to enable an expert to analyze NDT data via the cloud 24. In one embodiment, an application containing computer instructions executable by the cloud 24 may be accessed using the mobile device 22, the client-side computing device 274, and/or the computing system 29 to perform the process 390. Although the process 390 depicts a particular order in which the process 390 may be performed, it should be noted that the process 390 may also be performed in a different order.

As such, at block 392, the application may receive user identification information such as a login name, password, or the like. Based on the received user identification information, the application may, at block 394, generate a layout and/or data analysis tools for the expert. That is, the application may generate a layout or present the NDT data according to a layout that may have been specified as a preference by the expert. In one embodiment, the application may generate a layout that may organize the NDT data according to its type, date received, identification number, or the like. In this manner, the expert may be provided a comprehensive view of the NDT data available to be analyzed. In another embodiment, the application may generate a layout based on the process described above with respect to block 3374 of FIG. 19.

In addition to or lieu of generating the layout, the application may import a set of data analysis tools based on the user identification information. That is, the application may determine the set of data analysis tools that may be defined as a preference for the user. Alternatively, the set of data analysis tools may be generated or imported according to the process described above with respect to block 386 of FIG. 20.

After generating and displaying the layout and/or the data analysis tools, the application may, at block 396, receive a request or indication from the expert to analyze NDT data. As such, the expert may provide an input to the application using an input device that may indicate a particular set of NDT data to be analyzed. At block 398, the application may implement a user workflow that may be used to analyze or review the selected NDT data.

The user workflow may be determined based on a template that may be accessible by the cloud 24. The cloud 24 may have access to a number of user workflows and the application may display each user workflow to the expert. The expert may then select a user workflow to use to analyze the NDT data. In certain embodiments, the user workflow may have been created by the expert using an application-building tool that may be designed to create a data analysis workflow to review and analyze the NDT data.

Alternatively, the user workflow may be imported via the NDT data. That is, the application may use a particular user workflow for each type of NDT data, and the user workflow may be defined in the metadata of the NDT data. For example, the NDT data may have been acquired using a particular inspection workflow that may have assisted the NDT inspector 276 in performing his inspection. The inspection workflow may have been generated by an expert or the like using an application-building tool to define a process in which an inspection in the NDT system 10 may be performed. The inspection workflow may be associated with a particular user workflow that may be used to analyze the NDT data. In this case, the metadata of the acquired NDT data may indicate that the NDT data was acquired using the particular inspection workflow and may also indicate the association between the particular inspection workflow and the respective user workflow.

Keeping this in mind, the user workflow may be a part of an overall workflow definition along with the inspection workflow. As such, in certain embodiments, the overall workflow definition may be sent to an NDT inspection device 12. The NDT inspector 276 may then access the inspection workflow via the NDT inspection device 12 to guide him through his inspection process. As the NDT data is acquired by the NDT inspection device 12, the NDT data may be modified to include metadata that defines the overall workflow, including the inspection workflow and the user workflow that may be used to analyze the acquired NDT data. When the NDT data is accessed later by an expert or the like for review and/or analysis, the application may access the metadata of the NDT data to determine an appropriate user workflow to implement for the review and/or analysis of the NDT data. As mentioned above, the user workflow may specify a layout in which to display the NDT data, a set of data analysis tools, pre-configuration algorithms, and the like.

After the NDT data has been analyzed and/or reviewed, the application may generate a report that may summarize the analyzed NDT data. The report may also include a summary of the user workflow implemented when analyzing the particular NDT data, a summary of the inspection workflow used to acquire the particular NDT data, or the like. The report may include modified versions of the NDT data at different stages in the workflow. After generating the report, the application may send the report to one or more individuals or to the database 272. The recipients of the report may be specified by the user of the application, within the workflow, or the like.

Technical effects of the systems and techniques described herein include automatically retrieving data fields or reporting entries related to the assets currently being inspected. As such, the NDT inspector 276 may more efficiently perform the inspection process. Moreover, since the relevant information may also include additional or supplemental information related to the data being shared, the NDT inspector 276 and the NDT 278 may more effectively analyze and troubleshoot problems that may arise during the inspection process by quickly consulting the relevant information.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A collaboration system, comprising:
a first computing device configured to communicate with at least one other computing device via a computing network, wherein the computing network is configured to communicatively couple a plurality of computing devices and wherein the first computing device is configured to:
receive data that has been acquired using one or more non-destructive testing (NDT) inspection devices;
establish a communication connection between the first computing device and the at least one other computing device, wherein the communication connection is configured to share data depicted on the first computing device with the at least one other computing device;
determine a first amount of time since an inspection process started;
compare the first amount of time with a second amount of time, wherein the second amount of time is determined based on empirical data associated with a previously performed inspection process;
estimate location information of the one or more NDT inspection devices based on the comparison;
determine a type of one or more assets that correspond to the data based on the location information, wherein the one or more assets comprise parts within one or more turbomachinery components being inspected using the one or more NDT inspection devices;
identify information associated with the assets; and
display the information.

2. The collaboration system of claim 1, wherein the data comprises a live video feed that corresponds to the one or more NDT inspection devices.

3. The collaboration system of claim 1, wherein the first computing device is configured to identify a portion of the inspection process.

4. The collaboration system of claim 3, wherein the information related to the inspection process comprises an amount of time in which the inspection process has been in progress, workflow information or other empirical data related to the inspection process employed by the respective user, or any combination thereof.

5. The collaboration system of claim 1, comprising one or more location determining devices configured to determine the location information.

6. The collaboration system of claim 1, wherein the assets comprise one or more components of equipment in a NDT system, wherein the components are inspected using the one or more NDT inspection devices.

7. The collaboration system of claim 1, wherein the first computing device is configured to display one or more data fields associated with the assets, wherein the one or more data fields are configured to receive one or more entries by a user of the computing device or the at least one other computing device.

8. The collaboration system of claim 1, wherein the information related to the assets comprise previous inspection data for the assets, inspection data for other assets substantially similar to the assets, measurement information for the assets, measurement limits for the assets, service bulletins or updates for the assets, technical manuals or updated technical manuals for the assets, original equipment manufacturer (OEM) recommendations for the assets, or any combination thereof.

9. The collaboration system of claim 1, wherein the information related to the assets is stored on a database that is configured to be communicatively coupled to the computing network.

10. A computing device comprising a non-transitory computer readable medium comprising program instructions configured to be executed by a processor, wherein the program instructions are configured to:
receive, via the processor, data that has been acquired using one or more non-destructive testing (NDT) inspection devices;
establish, via the processor, a communication connection between the computing device and at least one other computing device in a computing network, wherein the communication connection is configured to share data depicted on the computing device with the at least one other computing device;
determine a first amount of time since an inspection process started;
compare the first amount of time with a second amount of time, wherein the second amount of time is determined based on empirical data associated with a previously performed inspection process;
estimate location information of the one or more NDT inspection devices based on the comparison;
determine, via the processor, a type of one or more assets that correspond to the data based on the location information, wherein the one or more assets are associated with one or more parts within one or more turbomachinery components being inspected using the one or more NDT inspection devices; and
retrieve, via the processor, information associated with the assets from a database based on the type of the one or more assets, wherein the database is configured to be communicatively coupled to the computing network.

11. The computing device of claim 10, wherein the program instructions are configured to retrieve the information by:
displaying, via the processor, one or more graphical user interface (GUI) graphics configured to receive an input, wherein the GUI graphics indicate that the information associated with the assets is available; and
displaying, via the processor, the information when the input is received.

12. The computing device of claim 11, wherein the information is stored, via the processor, on the computing device, the at least one other computing device, the database, or any combination thereof.

13. A non-transitory computer readable medium comprising instructions configured to:
receive data that has been acquired using one or more non-destructive testing (NDT) inspection devices;
establish a communication connection with at least one other computing device in a computing network, wherein the communication connection is configured to share the data with the at least one other computing device;

recognize one or more parts within one or more turbomachinery components being inspected by the NDT inspection devices based on one or more images from the one or more NDT inspection devices using image recognition;

determine location information within the one or more turbomachinery components based on the one or more parts; and identify asset information associated with the assets, wherein the information comprises one or more service bulletins for the assets, one or more updates for the assets, one or more technical manuals for the assets, one or more updated technical manuals for the assets, one or more original equipment manufacturer (OEM) recommendations for the assets, or any combination thereof; and display the location information and the asset information.

14. The non-transitory computer readable medium of claim 13, wherein instructions configured to determine the location information comprises comparing the data and information related to an inspection process that corresponds to the data.

15. The non-transitory computer readable medium of claim 14, wherein comparing the data and the information related to the inspection process comprises:

determining an amount of time since the inspection process started;

comparing the amount of time with empirical data associated with the inspection process; and estimating the location information based on the comparison.

16. The non-transitory computer readable medium of claim 15, wherein the empirical data corresponds to one or more previous inspections performed on equipment associated with the data using the one or more NDT inspection devices.

17. The non-transitory computer readable medium of claim 13, wherein the data comprises a live video feed acquired by the one or more NDT inspection devices.

18. The non-transitory computer readable medium of claim 17, wherein the location information is determined by using image recognition technology on the one or more images acquired by the live video feed.

19. The collaboration system of claim 1, wherein the first computing device is configured to determine one or more useful life values associated with the one or more assets based on the data.

20. The collaboration system of claim 1, wherein the information is associated with one or more compressors, one or more combustion chambers, one or more turbines, or any combination thereof.

* * * * *